US009185950B2

(12) United States Patent
Dobrin et al.

(10) Patent No.: US 9,185,950 B2
(45) Date of Patent: Nov. 17, 2015

(54) SHAPED FASTENING SYSTEMS FOR USE WITH ABSORBENT ARTICLES

(71) Applicant: The Procter & Gamble Company, Cincinnati, OH (US)

(72) Inventors: George Christopher Dobrin, Mason, OH (US); Amy Lynn Tally, Cold Spring, KY (US); Elizabeth Ann Peterson, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 175 days.

(21) Appl. No.: 14/063,273

(22) Filed: Oct. 25, 2013

(65) Prior Publication Data

US 2014/0121628 A1    May 1, 2014

Related U.S. Application Data

(60) Provisional application No. 61/718,470, filed on Oct. 25, 2012, provisional application No. 61/767,285, filed on Feb. 21, 2013.

(51) Int. Cl.
| *A61F 13/15* | (2006.01) |
|---|---|
| *A44B 18/00* | (2006.01) |
| *A61F 13/56* | (2006.01) |
| *A61F 13/62* | (2006.01) |
| *A61F 13/58* | (2006.01) |

(52) U.S. Cl.
CPC ............. *A44B 18/0003* (2013.01); *A61F 13/56* (2013.01); *A61F 13/565* (2013.01); *A61F 13/622* (2013.01); *A61F 2013/5683* (2013.01); *A61F 2013/5688* (2013.01); *A61F 2013/588* (2013.01); *Y10T 24/27* (2015.01); *Y10T 24/33* (2015.01); *Y10T 29/49* (2015.01)

(58) Field of Classification Search
CPC .................... A61F 13/49014; A61F 13/49015; A61F 13/5622; A61F 13/5633; A61F 13/565; A61F 13/58; A61F 13/62; A61F 13/622; A61F 13/625; A61F 2013/49047; A61F 2013/5683; A61F 2013/5688; A61F 2013/588
See application file for complete search history.

(56) References Cited

U.S. PATENT DOCUMENTS

| 3,848,594 A | 11/1974 | Buell |
|---|---|---|
| 3,860,003 A | 1/1975 | Buell |

(Continued)

FOREIGN PATENT DOCUMENTS

| EP | 0149880 A2 | 7/1985 |
|---|---|---|
| WO | WO 95/16746 A1 | 6/1995 |

(Continued)

OTHER PUBLICATIONS

International Search Report, PCT/US2013/066844, mailed Jan. 29, 2014, 6 pages.

(Continued)

*Primary Examiner* — Lynne Anderson
(74) *Attorney, Agent, or Firm* — Andrew J. Mueller; Andrew A Paul

(57) ABSTRACT

A fastening system comprising a closure member (tab) and one or more of an elastic/stretch member (ear), a release tape, and a landing member. The tabs and ears are divided into zones of certain dimensions. The angles at which the tabs transition the zones are defined. The system provides for improved fit of an absorbent article about the article's wearer.

68 Claims, 23 Drawing Sheets

(56) References Cited

U.S. PATENT DOCUMENTS

| | | |
|---|---|---|
| 4,610,678 A | 9/1986 | Weisman et al. |
| 4,662,875 A | 5/1987 | Hirotsu et al. |
| 4,834,735 A | 5/1989 | Alemany et al. |
| 4,846,815 A | 7/1989 | Scripps |
| 4,888,231 A | 12/1989 | Angstadt |
| 4,894,060 A | 1/1990 | Nestegard |
| 4,940,464 A | 7/1990 | Van Gompel et al. |
| 4,946,527 A | 8/1990 | Battrell |
| 5,037,416 A | 8/1991 | Allen et al. |
| 5,092,861 A | 3/1992 | Nomura et al. |
| 5,137,537 A | 8/1992 | Herron et al. |
| 5,151,092 A | 9/1992 | Buell et al. |
| 5,221,274 A | 6/1993 | Buell et al. |
| 5,246,433 A | 9/1993 | Hasse et al. |
| 5,260,345 A | 11/1993 | DesMarais et al. |
| 5,269,775 A | 12/1993 | Freeland et al. |
| 5,358,500 A | 10/1994 | Lavon et al. |
| 5,387,207 A | 2/1995 | Dyer et al. |
| 5,397,316 A | 3/1995 | LaVon et al. |
| 5,554,145 A | 9/1996 | Roe et al. |
| 5,569,234 A | 10/1996 | Buell et al. |
| 5,571,096 A | 11/1996 | Dobrin et al. |
| 5,603,794 A | 2/1997 | Thomas |
| 5,625,222 A | 4/1997 | Yoneda et al. |
| 5,873,870 A * | 2/1999 | Seitz et al. ............... 604/385.04 |
| 5,897,545 A | 4/1999 | Kline et al. |
| 5,957,908 A | 9/1999 | Kline et al. |
| 6,004,306 A | 12/1999 | Roe et al. |
| 6,120,487 A | 9/2000 | Ashton |
| 6,120,489 A | 9/2000 | Johnson et al. |
| 6,142,985 A * | 11/2000 | Feist ....................... 604/385.28 |
| 6,251,097 B1 | 6/2001 | Kline et al. |
| 6,432,098 B1 | 8/2002 | Kline et al. |
| 6,645,569 B2 | 11/2003 | Cramer et al. |
| 6,669,618 B2 | 12/2003 | Reising et al. |
| 6,863,933 B2 | 3/2005 | Rohrbaugh et al. |
| 7,112,621 B2 | 9/2006 | Rohrbaugh et al. |
| 7,371,302 B2 | 5/2008 | Miyamoto et al. |
| 8,168,853 B2 | 5/2012 | Autran et al. |
| 8,193,407 B2 | 6/2012 | Mansfield et al. |
| 8,226,626 B2 | 7/2012 | Turner et al. |
| 8,419,702 B2 * | 4/2013 | Shimizu et al. ............... 604/389 |
| 2003/0105190 A1 | 6/2003 | Diehl et al. |
| 2003/0148684 A1 | 8/2003 | Cramer et al. |
| 2003/0233082 A1 | 12/2003 | Kline et al. |
| 2004/0022998 A1 | 2/2004 | Miyamoto et al. |
| 2004/0158212 A1 | 8/2004 | Ponomarenko et al. |
| 2004/0181200 A1 | 9/2004 | Desai et al. |
| 2004/0193133 A1 | 9/2004 | Desai et al. |
| 2005/0008839 A1 | 1/2005 | Cramer et al. |
| 2005/0159720 A1 | 7/2005 | Gentilcore et al. |
| 2007/0078427 A1 | 4/2007 | Raycheck et al. |
| 2007/0093769 A1 | 4/2007 | Kline et al. |
| 2007/0219521 A1 | 9/2007 | Hird et al. |
| 2010/0036339 A1 | 2/2010 | Hammons et al. |
| 2010/0036347 A1 | 2/2010 | Hammons et al. |
| 2010/0036349 A1 | 2/2010 | Hammons et al. |
| 2010/0280484 A1 | 11/2010 | Kline et al. |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0139662 A1 | 6/2011 | Hird et al. |
| 2011/0152812 A1 | 6/2011 | Hird et al. |

FOREIGN PATENT DOCUMENTS

| | | |
|---|---|---|
| WO | WO 96/19169 | 6/1996 |
| WO | WO 02/064877 A2 | 8/2002 |
| WO | WO 2005/110731 A2 | 11/2005 |

OTHER PUBLICATIONS

U.S. Appl. No. 14/063,458, filed Oct. 25, 2013, George Christopher Dobrin.

* cited by examiner

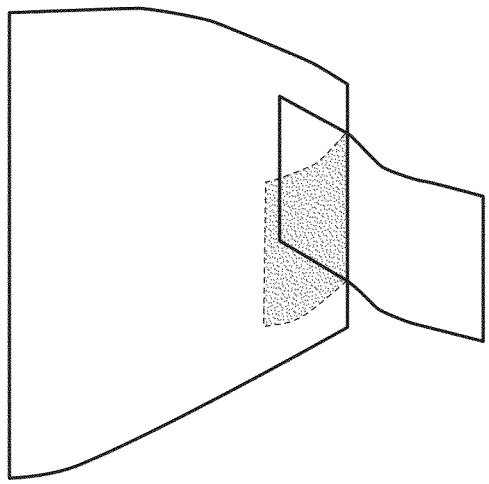
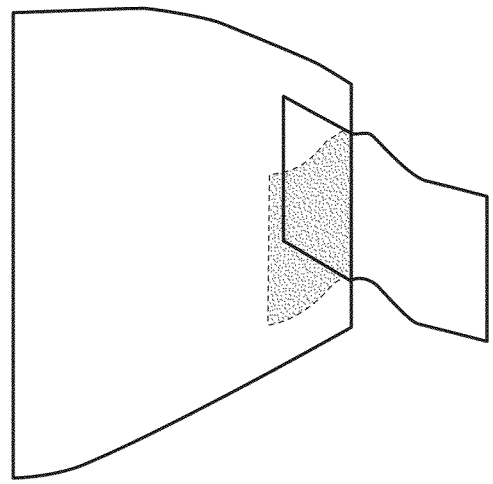
Fig. 9C                          Fig. 9D

SHAPED FASTENING SYSTEMS FOR USE WITH ABSORBENT ARTICLES

TECHNICAL FIELD

The present disclosure relates to articles with fastening systems, and more particularly relates to wearable absorbent articles with fastening systems having certain shapes that improve the fit of such articles about a wearer, where such systems may be refastenable.

BACKGROUND

The use of fastening systems for securing the corners of disposable absorbent articles, such as diapers, is known. Such systems are used to provide a secure means for keeping such articles on the wearer during use. When such systems are refastenable, adjustments may be made during use to reposition the articles, to allow a caregiver to check for soiling, and may also be used to provide a secure means for keeping such articles and their soiled contents wrapped up after use until disposal.

A typical fastening system for use with absorbent articles may have a closure member (tab) and a landing member. The closure member (tab) may be disposed directly or indirectly upon the longitudinal edge of the body portion in either the front or back of the absorbent article waist regions. In use, the closure member (tab) may be secured to the landing member, which is disposed upon the correspondingly opposite body portion of the front or back of the absorbent article. A refastenable system may be provided with, e.g., hooks on the closure member (tab) that releasably engage loops disposed on the landing member. To improve fit, the end of the closure member (tab) that does not engage the loops in the landing member area, may be attached to one end of an elastic/stretch member (ear), and the other end of the elastic/stretch member may be secured to the longitudinal edge of the body portion of the absorbent article.

The inventors have found that after fastening, conventional absorbent articles having an elastic/stretch member (ear) connected to a closure feature (tab) have a tendency to neither distribute forces evenly within the elastic/stretch member (ear), nor adequately to provide sustained comfortable fit to the wearer. This is particularly apparent when the closure feature (tab) (of higher modulus) and the elastic/stretch member (ear) (of lower modulus), which together provide the force required and line of tension required to hold the absorbent article about the wearer, have an incomplete attachment in the vertical (relative to the wearer) direction. Modulus as described here refers to Young's modulus, typically described in units of either $N/m^2$ or $lbs/in^2$, and higher/lower means relative to each other. In this case, the closing of the closure system imparts a force through the high modulus portion of the closure system into and through the elastic/stretch member. Typically, the attachment of the closure feature (tab) to the elastic/stretch member (ear) is centered about the height of the closure feature (tab) along the line of attachment to the elastic/stretch member (ear). As the closure member (tab) is typically smaller in area than the elastic/stretch member (ear) and even then, only a portion of the closure member (tab) engages the elastic/stretch member, the areas of the elastic/stretch member (ear) that are attached to the higher modulus closure feature (tab) do not exhibit the same force or strain profile as those areas which are not attached to it. Without being bound by theory, Applicants believe that the impact on fit and comfort is that this causes tension lines to develop which can lead to localized discomfort and red marking due to the presence of rigidity caused by high tension bands.

Additionally, and again without wishing to be bound by theory, Applicants believe the elastic/stretch material (ear) in the conventional arrangement will, a la the Poisson effect, tend to rope and collapse to the height of the high modulus closure feature (tab), leading to reduced surface area coverage and less contact area for friction lock of the elastic/stretch member (ear) on the wearer's body for fit. On the molecular level, Poisson's effect is caused by slight movements between molecules and the stretching of molecular bonds within the material lattice to accommodate the stress. When the bonds elongate in the direction of load, they shorten in the other directions. Without being limited by theory, it is believed that this behavior multiplied many times throughout the material lattice is what drives the phenomenon.

Attempts to achieve good fit have been made previously; however, there is a need to improve over these. For example, U.S. Pat. No. 5,358,500 (Lavon, et al.) discloses tape tabs secured to a landing member that are shaped and oriented to provide a primary line of tension through the diaper at an angle to the lateral direction. However, it is desirable to direct more force than these tape tabs (which are angled in the portion of the tab not connected to the ear, but rectangular and straight in the portion of the tab connected to the ear) provide to the top area of the ear, and thereby, to the top/back of the diaper, to promote a more snug fit to the wearer. Also, U.S. Pat. No. 5,603,794 (Thomas) discloses angled tape tabs for use with disposable absorbent articles. However, it is desirable to direct more force than these angled tape tabs (which lack an intermediate portion that is whose top and bottom edges are not in-line with the top and bottom edges of the portion of the tab not connected to the ear and the portion of the tab connected to the ear) provide to the top area of the ear, and thereby, to the top/back of the diaper, to promote a more snug fit to the wearer. As such, there is a need for fastening systems that provide improved fit to the wearers of absorbent articles.

SUMMARY

A fastening system comprising a closure member (tab) and one or more of an elastic/stretch member (ear), a release tape, and a landing member. The tabs and ears are divided into zones of certain dimensions. The angles at which the tabs transition the zones are defined. The system provides for improved fit of an absorbent article about the article's wearer.

BRIEF DESCRIPTION OF THE DRAWINGS

FIGS. 9A, 9B, 9C, and 9D are plan views of a fastening system comprising an elastic/stretch member (ear) with a closure member (tab) and a release tape.

DETAILED DESCRIPTION

Definitions

Figure 1:
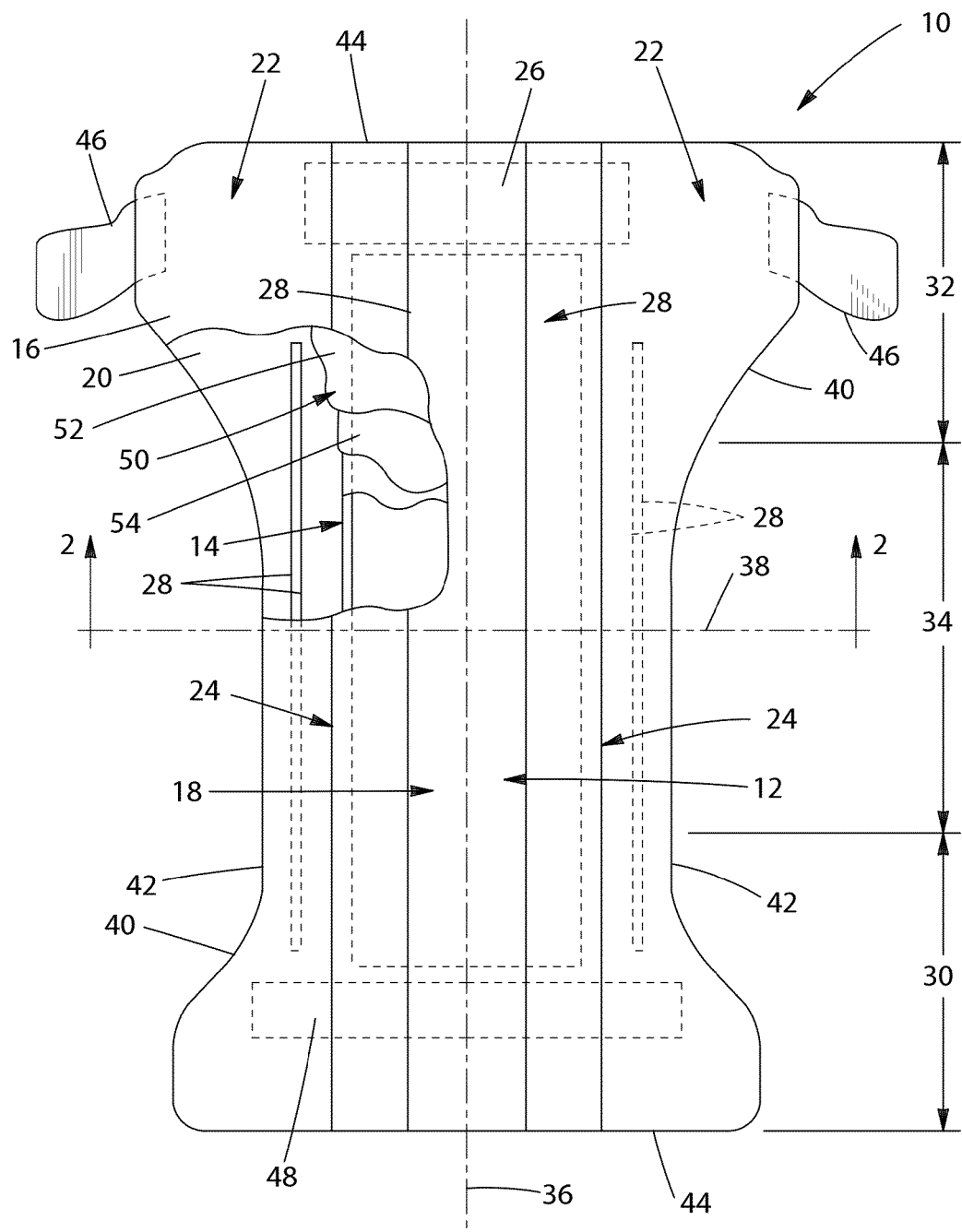
FIG. 1 is a plan view of a diaper.

The following term explanations may be useful in understanding the present disclosure.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure that may be disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core may be substantially cellulose free. The absorbent core does not include an acquisition system, a topsheet, or a backsheet of the absorbent article.

"Absorbent polymer material," "absorbent gelling material," "AGM," "superabsorbent," and "superabsorbent material" are used interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" means an absorbent polymer material which is in particulate form so as to be flowable in the dry state.

"Absorbent particulate polymer material area" means the area of the core wherein the first substrate and second substrate are separated by a multiplicity of superabsorbent particles. There may be some extraneous superabsorbent particles outside of this area between the first substrate 64 and second substrate.

"Activation" means any process by which tensile strain produced by intermeshing teeth and grooves causes intermediate web sections to stretch or extend. Such processes have been found useful in the production of many articles including breathable films, stretch composites, apertured materials and textured materials. For nonwoven webs, the stretching can cause fiber reorientation, change in fiber denier and/or cross section, a reduction in basis weight, and/or controlled fiber destruction in the intermediate web sections. For example, a common activation method is the process known in the art as ring rolling.

"Airfelt" means comminuted wood pulp, which is a form of cellulosic fiber.

"Basis weight" means the mass of dry fibrous material per unit area, i.e. the mass of dry sheet per unit area, e.g. gram per square meter (gsm).

"Body facing surface" and "body facing side" refer to surfaces of absorbent articles and/or components thereof which face a wearer's body when the absorbent articles are worn, and the term "garment facing surface" and "garment facing side" refer to surfaces of absorbent articles and/or components thereof that face away from a wearer's body when the absorbent articles are worn. Absorbent articles and components thereof, including the topsheet, backsheet, absorbent core, and any individual materials of their components, have a body facing surface and/or side and a garment facing surface and/or side.

"Bicomponent fibers" means fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" means an absorbent article generally worn by infants and incontinent persons about the lower torso so as to encircle the waist and legs of the wearer and that is specifically adapted to receive and contain urinary and fecal waste. As used herein, term "diaper" also includes a "pant" which is defined below.

"Fiber" and "filament" are used interchangeably.

"Film" means a skin-like or membrane-like layer of material formed of one or more polymers, which does not have a form consisting predominately of a web-like structure of consolidated polymer fibers and/or other fibers.

"Inboard", and forms thereof, with respect to features of a fastening member, means furthest from or in a direction away from the free distal end.

"Joined" is meant to encompass configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" means a direction running from a longitudinally extending side edge to a laterally opposing longitudinally extending side edge of an article and generally at a right angle to the longitudinal direction. Directions within 45 degrees of the lateral direction are considered to be "lateral."

"Machine direction" (MD) means the direction of material flow through a process. In addition, relative placement and movement of material can be described as flowing in the machine direction through a process from upstream in the process to downstream in the process. "Cross direction" (CD) means a direction that is generally perpendicular to the machine direction. "Z-direction," with respect to a web, means generally orthogonal or perpendicular to the plane approximated by the web along the machine and cross direction dimensions.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Outboard", and forms thereof, with respect to features of a fastening member, means at or in a direction toward its free distal end.

"Pant" or "training pant" means disposable garments having a waist opening and leg openings designed for infant or adult wearers. A pant may be placed in position on the wearer by inserting the wearer's legs into the leg openings and sliding the pant into position about a wearer's lower torso. A pant may be pre-formed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" means an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" indicates that within the absorbent particulate polymer material area, the first substrate 64 and second substrate 72 are separated by a multiplicity of superabsorbent particles. It is recognized that there may be minor incidental contact areas between the first substrate 64 and second substrate 72 within the absorbent particulate polymer material area. Incidental contact areas between the first substrate 64 and second substrate 72 may be intentional or unintentional (e.g. manufacturing artifacts) but do not form geometries such as pillows, pockets, tubes, quilted patterns and the like.

"Tensile Strength" refers to the maximum tensile force (Peak Force) a material will sustain before tensile failure, as measured by the Tensile Strength Measurement Method set forth herein.

"Thermoplastic adhesive material" is understood to comprise a polymer composition from which fibers are formed and applied to the superabsorbent material with the intent to immobilize the superabsorbent material in both the dry and wet state. The thermoplastic adhesive material of the present disclosure forms a fibrous network over the superabsorbent material.

"Thickness" and "caliper" are used herein interchangeably.

In some embodiments, the absorbent article is a diaper. For convenience, an exemplary absorbent article will be described using a diaper as a reference. The skilled person will appreciate that other absorbent articles can also be assembled with topsheets and associated components as disclosed herein.

FIG. 1 is a plan view of a diaper 10, shown in a flat out, uncontracted state (i.e., without elastic induced contraction) and with portions of the diaper 10 are cut away to more clearly show the underlying structure of the diaper 10. A portion of the diaper 10 that contacts a wearer is facing the viewer in FIG. 1. The diaper 10 generally may include a chassis 12 and an absorbent core 14 disposed in the chassis.

The chassis 12 of the diaper 10 in FIG. 1 may include an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each include elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with a longitudinal axis 36 and a transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing member 48.

The diaper 20 may also include such other features as are known in the art including front and rear ear panels, waist cap features, elastics and the like to provide better fit, as well as containment and aesthetic characteristics. Such additional features are described, for example, in U.S. Pat. Nos. 3,860,003 and 5,151,092.

In order to keep the diaper 10 in place about the wearer, at least a portion of the first waist region 30 may be attached by the fastening member 46 to at least a portion of the second waist region 32 to form leg opening(s) and an article waist opening. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

Fastening member 46 is adapted to refastenably connect with the first waist region 30. As such, the fastening member 46 may include various types of refastenably engageable fasteners and various types of refastenable fastening structures. For example, fastening member 46 may include mechanical fasteners, in the form of hook and loop fasteners, hook and hook fasteners, macrofasteners, buttons, snaps, tab and slot fasteners, tape fasteners, adhesive fasteners, cohesive fasteners, magnetic fasteners, hermaphroditic fasteners, and the like. Some examples of fastening systems and/or fastening components are discussed in U.S. Pat. Nos. 3,848,594; 4,662,875; 4,846,815; 4,894,060; 4,946,527; 5,151,092; 5,221,274; 6,251,097; 6,669,618; 6,432,098; and U.S. Patent Publication Nos. 2007/0078427 and 2007/0093769.

In some embodiments, the diaper 10 may be provided with a re-closable fastening system or may alternatively be provided in the form of a pant-type diaper. When the absorbent article is a diaper, it may include a re-closable fastening system joined to the chassis for securing the diaper to a wearer. When the absorbent article is a pant-type diaper, the article may include at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. In some embodiments, the materials making up the fastening device may be flexible. The flexibility may allow the fastening system to conform to the shape of the body and thus, reduce the likelihood that the fastening system will irritate or injure the wearer's skin.

It is to be appreciated that the topsheet 18, the backsheet 20, and the absorbent core 14 may be assembled in a variety of configurations, such as for example as described generally in U.S. Pat. Nos. 5,554,145; 5,569,234; and 6,004,306. Processes for assembling the diaper include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company (St. Paul, Minn.) under the designation HL-1258 or H-2031.

In some embodiments, the topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. Nos. 5,037,416 and 5,269,775.

The backsheet 26 may be joined with the topsheet 18. The backsheet 20 may prevent the exudates absorbed by the absorbent core 14 and contained within the diaper 10 from soiling other external articles that may contact the diaper 10, such as bed sheets and undergarments. In certain embodiments, the backsheet 26 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind., and sold under the trade names X15306, X10962, and X10964. Other suitable backsheet materials may include breathable materials that permit vapors to escape from the diaper 10 while still preventing liquid exudates from passing through the backsheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096.

Figure 2:
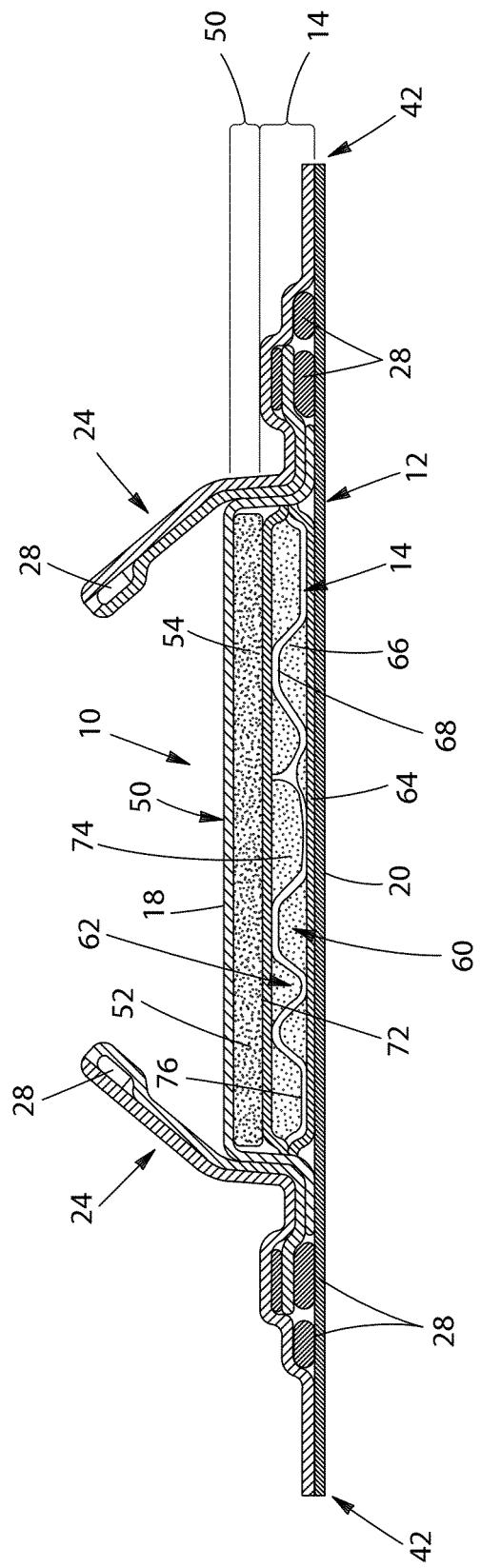
FIG. 2 is a cross sectional view of the diaper shown in FIG. 1 taken along the sectional line 2-2 of FIG. 1.

FIG. 2 is a cross sectional view of the diaper in FIG. 1 taken along the line 2-2. As shown in FIG. 2, the topsheet 18 may define an inner, body facing surface, and the backsheet may define an outer, garment facing surface of the diaper 10. And the absorbent core 14 may be positioned between the topsheet and the backsheet. The diaper 10 may also include an acquisition system 50 disposed between the liquid permeable topsheet 18 and a wearer facing side of the absorbent core 14. The acquisition system 50 may be in direct contact with the absorbent core. The acquisition system 50 (also referred to herein as a liquid acquisition layer 50) may comprise a single layer or multiple layers, such as an upper acquisition layer 52 (also referred to herein as a first acquisition layer 52) facing towards the wearer's skin and a lower acquisition layer 54 (also referred to herein as a second acquisition layer 54) facing the garment of the wearer. In some embodiments, the acquisition system 50 may function to receive a surge of liquid, such as a gush of urine. In other words, the acquisition system 50 may serve as a temporary reservoir for liquid until the absorbent core 14 can absorb the liquid.

In some embodiments, the acquisition system 50 may include chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between 0.5 mole % and 10.0 mole % of a $C_2$ to $C_9$ polycarboxylic cross-linking agent or between 1.5 mole % and 6.0 mole % of a $C_2$ to $C_9$ polycarboxylic cross-linking agent based on glucose unit. Citric acid is an exemplary cross-linking agent. In some embodiments, polyacrylic acids may be used. Further, according to some embodiments, the cross-linked cellulosic fibers have a water retention value of 25 to 60, or 28 to 50, or 30 to 45. A method for determining water retention value is disclosed in U.S. Pat. No. 5,137,537. In some embodiments, the cross-linked cellulosic fibers may be crimped, twisted, or curled, or a combination thereof including crimped, twisted, and curled.

In some embodiments, one or both of the upper acquisition layer 52 and lower acquisition layer 54 may include a non-woven, which may be hydrophilic. Further, according to some embodiments, one or both of the upper acquisition layer 52 and lower acquisition layer 54 may comprise the chemically cross-linked cellulosic fibers, which may or may not form part of a nonwoven material. In some embodiments, the upper acquisition layer 52 may comprise a nonwoven, without the cross-linked cellulosic fibers, and the lower acquisition layer 54 may comprise the chemically cross-linked cellulosic fibers. Further, in some embodiments, the lower acquisition layer 54 may comprise the chemically cross-linked cellulosic fibers mixed with other fibers such as natural or synthetic polymeric fibers. According to some embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. In some embodiments, the lower acquisition layer 54 has a total dry weight, the cross-linked cellulosic fibers are present on a dry weight basis in the upper acquisition layer in an amount from 30% to 95% by weight of the lower acquisition layer 54, and the other natural or synthetic polymeric fibers are present on a dry weight basis in the lower acquisition layer 54 in an amount from 70% to 5% by weight of the lower acquisition layer 54. According to some embodiments, the cross-linked cellulosic fibers are present on a dry weight basis in the first acquisition layer in an amount from 80% to 90% by weight of the lower acquisition layer 54, and the other natural or synthetic polymeric fibers are present on a dry weight basis in the lower acquisition layer 54 in an amount from 20% to 10% by weight of the lower acquisition layer 54.

For example, in some embodiments, the lower acquisition layer 54 may comprise 70% by weight of chemically cross-linked cellulose fibers, 10% by weight polyester (PET), and 20% by weight untreated pulp fibers. According to a second embodiment, the lower acquisition layer 54 may comprise 70% by weight chemically cross-linked cellulose fibers, 20% by weight lyocell fibers, and 10% by weight PET fibers. According to a third embodiment, the lower acquisition layer 54 may comprise 68% by weight chemically cross-linked cellulose fibers, 16% by weight untreated pulp fibers, and 16% by weight PET fibers. In one embodiment, the lower acquisition layer 54 may comprise from 90-100% by weight chemically cross-linked cellulose fibers.

Suitable nonwoven materials for the upper acquisition layer 52 and lower acquisition layer 54 include, but are not limited to SMS material, comprising a spunbonded, a meltblown and a further spunbonded layer. In certain embodiments, permanently hydrophilic nonwovens, and in particular, nonwovens with durably hydrophilic coatings are desirable. Another suitable embodiment comprises a SMMS-structure. In certain embodiments, the nonwovens are porous.

In certain embodiments, suitable nonwoven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720. Another way to produce nonwovens with durably hydrophilic coatings is to coat the nonwoven with hydrophilic nanoparticles as described in U.S. Pat. No. 7,112,621 and in PCT Publication No. WO 02/064877.

Nanoparticles may have a largest dimension of below 750 nm. Nanoparticles with sizes ranging from 2 to 750 nm may be economically produced. Some nanoparticles can be easily dispersed in water solution to enable coating application onto the nonwoven, form transparent coatings, and the coatings applied from water solutions are may be sufficiently durable to exposure to water. Nanoparticles can be organic or inorganic, synthetic or natural. Inorganic nanoparticles generally exist as oxides, silicates, and/or, carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated nonwoven is that disclosed in the U.S. Patent Publication No. 2004/0158212A1.

Other nonwovens are described in U.S. Pat. Nos. 6,645, 569; 6,863,933; and 7,112,621 as well as U.S. Patent Publication Nos. 2003/0148684A1 and 2005/0008839A1.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Permanently hydrophilic nonwovens may be used in other parts of an absorbent article. For example, in some embodiments, topsheets and absorbent core layers comprising permanently hydrophilic nonwovens as described above can be used.

According to some embodiments, the upper acquisition layer 52 may include a material that provides recovery when external pressure is applied and removed. Further, according to some embodiments, the upper acquisition layer 52 may comprise a blend of different fibers selected, for example from the types of polymeric fibers described above. In some embodiments, at least a portion of the fibers may exhibit a spiral-crimp which has a helical shape. In some embodiments, the upper acquisition layer 52 may comprise fibers having different degrees or types of crimping, or both. For example, embodiments may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to a 2D crimp or "flat crimp" and a 3D or spiral-crimp. According to some embodiments, the fibers may include bi-component fibers, which are individual fibers each comprising different materials, usually a first and a second polymeric material.

The upper acquisition layer 52 may be stabilized by a latex binder, for example a styrene-butadiene latex binder (SB latex), in a certain embodiment. Processes for obtaining such lattices are known, for example, from EP Patent Publication No. EP 0149880A2 and U.S. Patent Publication No. 2003/0105190. In some embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio).

Figure 3:
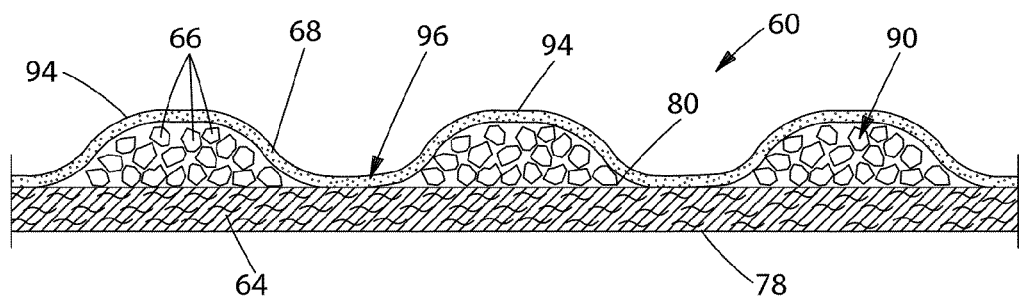
FIG. 3 is a partial cross sectional view of an absorbent core layer.

The absorbent core 14, such as shown in FIGS. 1-4, 5A, and 5B, may be disposed between the topsheet 18 and the backsheet 20 and may include two layers, a first absorbent layer 60 and a second absorbent layer 62. As shown in FIG. 3, the first absorbent layer 60 of the absorbent core 14 may include a substrate 64, an absorbent particular polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. According to another embodiment illustrated in FIG. 4, the first absorbent layer 60 of the absorbent core 14 may also include a cover layer 70 on the thermoplastic composition 68.

As shown in FIG. 2, the second absorbent layer 62 of the absorbent core 14 may also include a substrate 72, an absorbent particulate polymer material 74 on the second substrate 72, and a thermoplastic composition 66 on the absorbent particulate polymer material 74 and at least a portion of the second substrate 72 for immobilizing the absorbent particulate polymer material 74 on the second substrate 72. Although not illustrated, the second absorbent layer 62 may also include a cover layer such as the cover layer 70 illustrated in FIG. 4.

The substrate 64 of the first absorbent layer 60 may be referred to as a dusting layer and has a first surface 78 which faces the backsheet 20 of the diaper 10 and a second surface 80 which faces the absorbent particulate polymer material 66. The substrate 72 of the second absorbent layer 62 may be referred to as a core cover and has a first surface 82 facing the topsheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

In some embodiments, the substrates 64 and 72 of the first and second absorbent layers 60 and 62 may be a nonwoven material, such as those nonwoven materials described above. In some embodiments, the nonwovens are porous and may have a pore size of about 32 microns.

Figure 5A:
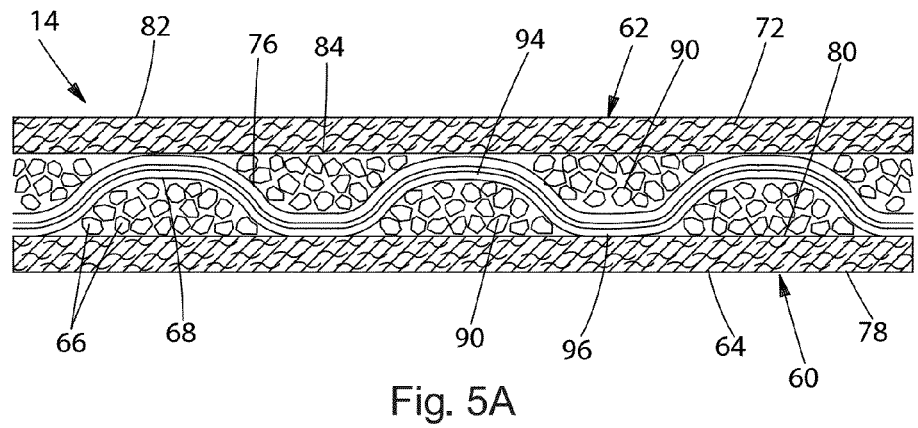
FIG. 5A is a partial sectional view of an absorbent core comprising a combination of first and second absorbent core layers described herein.
Figure 5B:
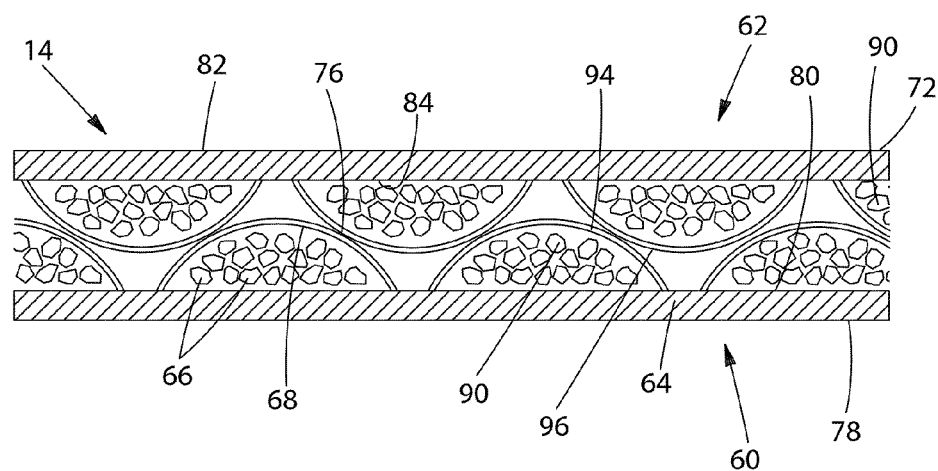
FIG. 5B is a partial sectional view of an absorbent core comprising a combination of the first and second absorbent core layers described herein.

As shown in FIGS. 5A, and 5B, the first and second layers 60 and 62 may be combined to form the absorbent core 14. The absorbent core 14 has an absorbent particulate polymer material area (not shown). The extent and shape of the absorbent particulate polymer material area may vary depending on the desired application of the absorbent core 14 and the particular absorbent article in which it may be incorporated. In some embodiments, the absorbent particulate polymer material area extends substantially entirely across the absorbent core 14. In some embodiments, absorbent particulate polymer material 66 and 74 is substantially continuously distributed across the absorbent particulate polymer material area.

The amount of absorbent particulate polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core 14 consists essentially of the first and second substrates 64 and 72, the absorbent particulate polymer material 66 and 74, and the thermoplastic adhesive composition 68 and 76. In some embodiments, the absorbent core 14 may be substantially cellulose free.

The absorbent particulate polymer material area may have a relatively narrow width in the crotch area of the absorbent article for increased wearing comfort. Hence, the absorbent particulate polymer material area may have a width as measured along a transverse line which is positioned at equal distance to the front edge and the rear edge of the absorbent article, which is less than about 100 mm, 90 mm, 80 mm, 70 mm, 60 mm or even less than about 50 mm.

It some absorbent articles, such as diapers, liquid discharge from the wearer may occur predominately in the front half of the diaper. The front half of the absorbent core 14 may therefore comprise most of the absorbent capacity of the core. Thus, according to certain embodiments, the front half of said absorbent core 14 may comprise more than about 60% of the superabsorbent material, or more than about 65%, 70%, 75%, 80%, 85%, or 90% of the superabsorbent material.

In certain embodiments, the absorbent core 14 may further comprise any absorbent material that is generally compressible, conformable, non-irritating to the wearer's skin, and capable of absorbing and retaining liquids such as urine and other certain body exudates. In such embodiments, the absorbent core 14 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 14 may further comprise minor amounts (typically less than about 10%) of materials, such as adhesives, waxes, oils and the like. Exemplary absorbent structures for use as the absorbent assemblies are described in U.S. Pat. Nos. 4,610,678; 4,834,735; 4,888,231; 5,260,345; 5,387,207; 5,397,316; and 5,625,222.

Figure 4:
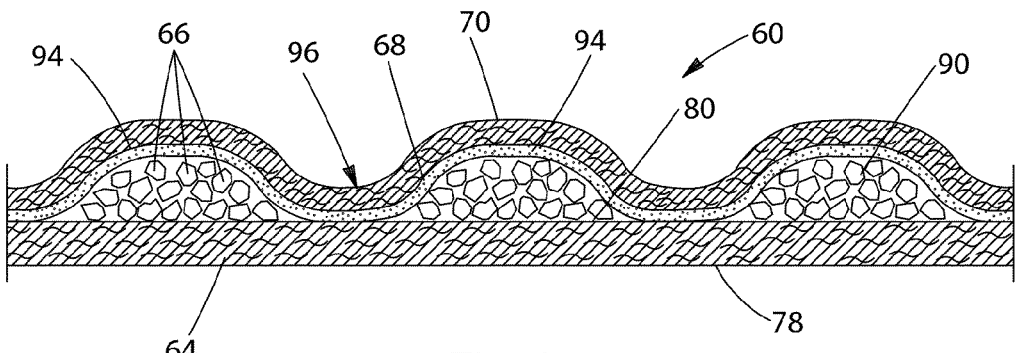
FIG. 4 is a partial cross sectional view of an absorbent core layer.

The thermoplastic adhesive material 68 and 76 may serve to cover and at least partially immobilize the absorbent particulate polymer material 66 and 74. In some embodiments, the thermoplastic adhesive material 68 and 76 can be disposed essentially uniformly within the absorbent particulate polymer material 66 and 74, between the polymers. In some embodiments, the thermoplastic adhesive material 68 and 76 may be provided as a fibrous layer which is at least partially in contact with the absorbent particulate polymer material 66 and 74 and partially in contact with the substrate layers 64 and 72 of the first and second absorbent layers 60 and 62. FIGS. 3 and 4 show such a structure wherein the absorbent particulate polymer material 66 and 74 is provided as a discontinuous layer, and a layer of fibrous thermoplastic adhesive material 68 and 76 is laid down onto the layer of absorbent particulate polymer material 66 and 74, such that the thermoplastic adhesive material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic adhesive material 68 and 76, which in itself is essentially a two-dimensional structure of relatively small thickness, as compared to the dimension in length and width directions. In other words, the thermoplastic adhesive material 68 and 76 undulates between the absorbent particulate polymer material 68 and 76 and the second surfaces of the substrates 64 and 72.

Thereby, the thermoplastic adhesive material 68 and 76 may provide cavities to cover the absorbent particulate polymer material 66 and 74, and thereby immobilizes this material. In a further aspect, the thermoplastic adhesive material 68 and 76 bonds to the substrates 64 and 72 and thus affixes the absorbent particulate polymer material 66 and 74 to the substrates 64 and 72. Thus, in accordance with certain embodiments, the thermoplastic adhesive material 68 and 76 immobilizes the absorbent particulate polymer material 66 and 74 when wet. Some thermoplastic adhesive materials will also penetrate into both the absorbent particulate polymer material 66 and 74 and the substrates 64 and 72, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive materials may also provide a very good immobilization of absorbent material when the absorbent core 14 is dry. The thermoplastic adhesive material 68 and 76 may also be referred to as a hot melt adhesive.

In accordance with certain embodiments, the thermoplastic adhesive material 68 and 76 may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer may have a molecular weight (Mw) of more than 10,000 and a glass transition temperature (Tg) usually below room temperature or −6° C.>Tg<16° C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of $C_2$ to $C_8$ alpha olefins.

In exemplary embodiments, the tackifying resin may have a Mw below 5,000 and a $T_g$ usually above room temperature, typical concentrations of the resin in a hot melt are in the range of about 30 to about 60%, and the plasticizer has a low Mw of typically less than 1,000 and a $T_g$ below room temperature, with a typical concentration of about 0 to about 15%.

In certain embodiments, the thermoplastic adhesive material 68 and 76 is present in the form of fibers. In some embodiments, the fibers may have an average thickness of about 1 to about 50 micrometers or about 1 to about 35 micrometers and an average length of about 5 mm to about 50 mm or about 5 mm to about 30 mm. To improve the adhesion of the thermoplastic adhesive material 68 and 76 to the substrates 64 and 72 or to any other layer, in particular any other nonwoven layer, such layers may be pre-treated with an auxiliary adhesive.

The absorbent core 14 may also comprise an auxiliary adhesive which is not illustrated in the figures. The auxiliary adhesive may be deposited on the first and second substrates 64 and 72 of the respective first and second absorbent layers 60 and 62 before application of the absorbent particulate polymer material 66 and 74 for enhancing adhesion of the absorbent particulate polymer materials 66 and 74 and the thermoplastic adhesive material 68 and 76 to the respective substrates 64 and 72. The auxiliary glue may also aid in immobilizing the absorbent particulate polymer material 66 and 74 and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary glue may be applied to the substrates 64 and 72 in various ways. For example, in some embodiments, the auxiliary glue may be applied in about 0.5 to about 1 mm wide slots spaced about 0.5 to about 2 mm apart.

The cover layer 70 shown in FIG. 4 may include the same material as the substrates 64 and 72, or may include a different material. In certain embodiments, the materials of the cover layer 70 are the nonwoven materials, such as the materials described above as useful for the substrates 64 and 72.

Although much of the present discussion is presented in the context of absorbent articles in form of diapers, it is to be appreciated that other absorbent articles, such as sanitary napkins can also be assembled with the topsheets and associated components as disclosed herein. Absorbent articles, such as sanitary napkins may be designed to be worn in close proximity to the crotch of the wearer. Such absorbent articles need to provide for fluid acquisition and retention and may look aesthetically pleasing, as well as be comfortable to wear. Examples of sanitary napkins are provided in U.S. Patent Publication Nos. 2010/0036339; 2010/0036347; and 2010/0036349, the disclosures of which are herein incorporated by reference. In use, sanitary napkins are stressed by a variety of fluid handling demands. Given the variety of fluid handling demands placed on different portions of an absorbent article, such as a sanitary napkin, the different physical interactions between portions of an absorbent article and portions of a wearer's body, and different moisture and chemical environments of different portions of a wearer's crotch region, there is continuing and unaddressed need for absorbent articles having aesthetically appealing, are comfortable to wear, but do not compromise the performance of the absorbent article. Sanitary napkins made with the topsheets described herein provide an aesthetically appealing surface to the body facing side of the article while not unduly compromising the performance of the acquisition layer and maintaining the comfort of the article during wearing.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing member nonwovens and film bases.

In at least one embodiment, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

Fastening Component

As described above, the disposable article may comprise a fastening member 46. Fastening member 46 may have a fastener zone that includes a fastener disposed at or near its outboard end. In one example, a fastener may be a patch of hook material constituting the hook components of a hook-and-loop fastening system. In this example, the garment-facing surface of the front waist region may have a laterally extended landing member bearing a patch or strip of loop material constituting the cooperating loop component of the hook-and-loop fastening system. Other examples may include any other cooperating engaging and receiving surfaces or components adapted to effect fastening, respective components of which may be disposed on either the fastening zone or the landing member, or another location of the absorbent article as desired, as long as they provide for the adjustability of the waist opening size and snugness of the absorbent article, e.g. diaper, as it is being applied to a wearer. Suitable components of fastening systems for use herein, methods of manufacture, and materials suitable for use are generally described in the following: USPA 2010/0280484A1, U.S. Pat. No. 8,226,626, U.S. Pat. No. 8,168,853, and U.S. Pat. No. 8,193,407. Examples of stretch laminates that may be suitable for forming the elastic/stretch member (ear) are described in WO 05/110731 and USPA Nos. US 2004/0181200 and US 2004/0193133.

Figure 6A:
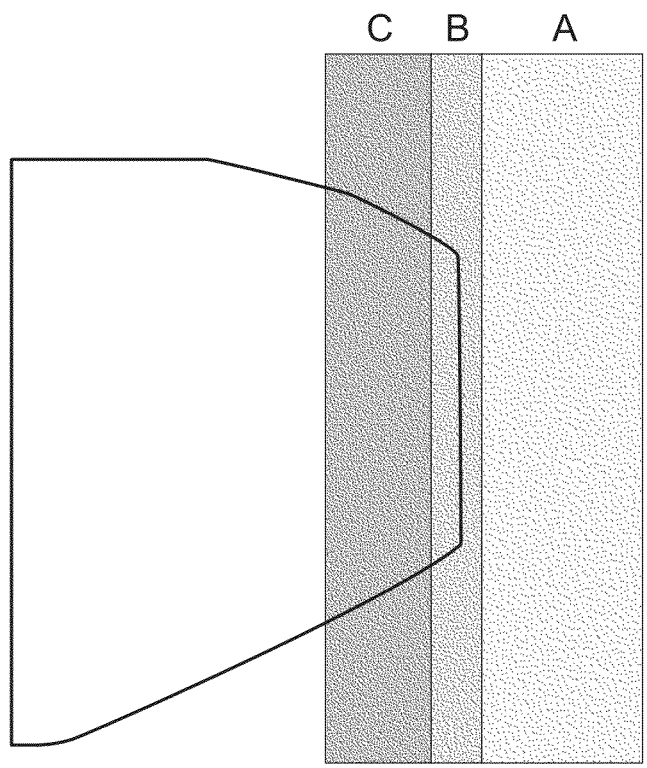
FIGS. 6A, 6B, and 6C are plan views of a fastening system comprising an elastic/stretch member (ear) with or without a closure member (tab), showing Tab Zones and Tab Angles.

The fastening system may comprise a closure member (tab). Referring to FIG. 6A, the closure member (tab) may be divided into 3 Tab Zones, characterized by the closure member's (tab) position when attached to an elastic/stretch member (ear). Tab Zone A is defined as the portion of the closure member (tab) that is not attached to nor lying in the same vertical plane as the elastic/stretch member (ear) (does not overlap at all), less the portion of Tab Zone B. Tab Zone C is defined as the portion of the closure member (tab) that is attached to and lies in the same vertical plane, when the member is laid flat in horizontal position, as viewed from above, as the elastic/stretch member (ear) (overlaps completely), less the portion of Tab Zone B. Tab Zone B occupies the transitional area between Tab Zone A and Tab Zone C, and is defined as a portion of the closure member (tab) which includes both a sub-portion that is not attached to nor lying in the same vertical plane, when the member is laid flat in horizontal position, as viewed from above, as the elastic/stretch member (ear) and a sub-portion that is attached to and lies in the same vertical plane, when the member is laid flat in horizontal position, as viewed from above, as the elastic/stretch member (ear) (partially overlaps). The Tab Zones are parallel to each other and their lateral borders are straight lines.

The primary functions of the portion of the closure member (tab) located within Tab Zone B include: (a) providing for a smooth and gradual arc/radius transition between the portions of the closure member (tab) located in Tab Zones A and C; and (b) providing preferred angles for the portions of the closure member (tab) located in Tab Zones A and B, to provide improved load distribution and fit while also providing the improved positioning of closure member (tab) on the front of the absorbent article (e.g. landing member). The preferred angle for Tab Zone A, if constant across Tab Zones B and C, would render the front position of the closure member too low for effective closure and/or for wearer comfort.

The width of Tab Zone A is typically from 18 to 38 mm, preferably from 20 to 35 mm, more preferably 20 to 25 mm. The width of Tab Zone B is typically from 2 to 20 mm, preferably from 5 to 20 mm, more preferably 5 to 15 mm. In some embodiments, the width of Tab Zone B will not be distributed symmetrically relative to the edge of the elastic/stretch member (ear) distal to the elastic/stretch member's (ear) attachment to the waist region of an absorbent article. For example, if the width of Tab Zone B is 8 mm, 2 mm may overlap the elastic/stretch member (ear) and 6 mm may not overlap it. In some embodiments, the width of Tab Zone B will be distributed symmetrically, and for the previous example, 4 mm may overlap the elastic/stretch member (ear) and 4 mm may not overlap it. The width of Tab Zone C is typically from 10 to 25 mm, preferably from 10 to 20 mm, more preferably 12 to 18 mm. The sum of the widths of the three Tab Zones (the total width) is typically from 35 to 55 mm, preferably from 40 to 50 mm, more preferably 45 to 50 mm. The length of each Tab Zone is typically from 25 to 50 mm, preferably from 25 to 45 mm, more preferably 28 to 40 mm.

Figure 6B:
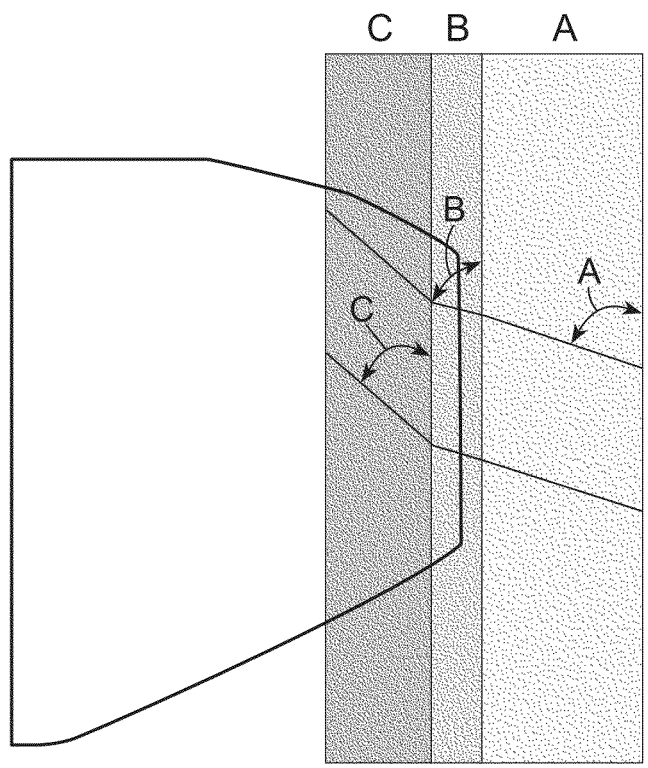
Figure 6C:
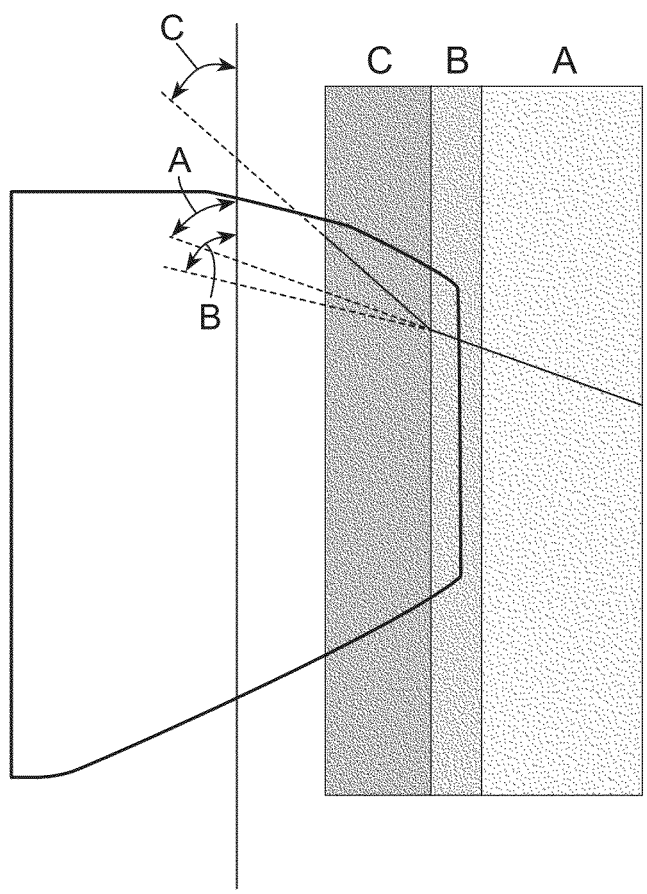

Referring to FIGS. 6B and 6C, the angle at which the closure member (tab) travels through each of the Tab Zones may be characterized by the closure member's (tab) position when attached to an elastic/stretch member (ear). Tab Angle A is defined as the angle between: (i) a line drawn from the point at which one edge of the closure member (tab) intersects the common border of Tab Zones A and B, and the point at which the same edge of the closure member (tab) intersects the other border of Tab Zone A; and (ii) a line drawn upon such other border of Tab Zone A. Tab Angle B is defined as the angle between: (i) a line drawn from the point at which one edge of the closure member (tab) intersects the common border of Tab Zones A and B, and the point at which the same edge of the closure member (tab) intersects the common border of Tab Zones B and C; and (ii) a line drawn upon the common border of Tab Zones A and B. Tab Angle C is defined as the angle between: (i) a line drawn from the point at which one edge of the closure member (tab) intersects the common border of Tab Zones B and C, and the point at which the same edge of the closure member (tab) intersects the other border of Tab Zone C; and (ii) a line drawn upon the common border of Tab Zones B and C.

In some embodiments, the Tab Angles for any given Tab Zone will be substantially the same or the same, whether measured using the edge of the closure member (tab) at the upper edge of the member, or at the lower edge of the member. Each Tab Angle is typically from 10 to 80°, preferably from 45 to 75°. Angles A and B, are each, independently, more preferably from 55 to 75°. In comparison to each other, Angle A is not equal to or substantially similar to Angle B, and/or, Angle B is not equal to or substantially similar to Angle C. In some embodiments, the difference between Angle A and Angle B is 5° or greater, preferably 10°. In some embodiments, Angle B is greater than Angle A. In some embodiments, the difference between Angle B and Angle C is 5° or greater, preferably 10°. In some embodiments, Angle B is greater than Angle C. In some embodiments, Angle B is greater than Angle A, which in turn, is greater than Angle C. As described above, in a preferred embodiment Angles A, B, and C, are not all equal to each other.

Figure 7A:
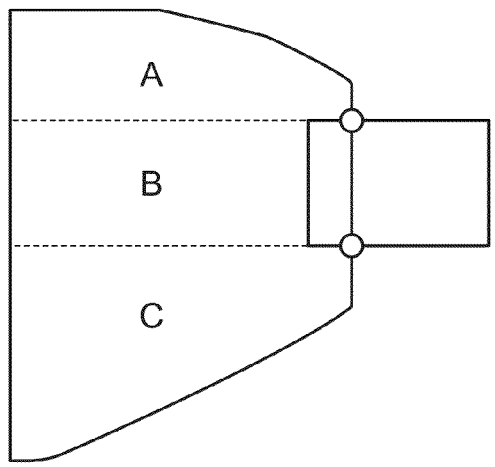
FIGS. 7A, 7B, and 7C are plan views of a fastening system comprising an elastic/stretch member (ear) with a closure member (tab), showing Ear Zones.
Figure 7B:
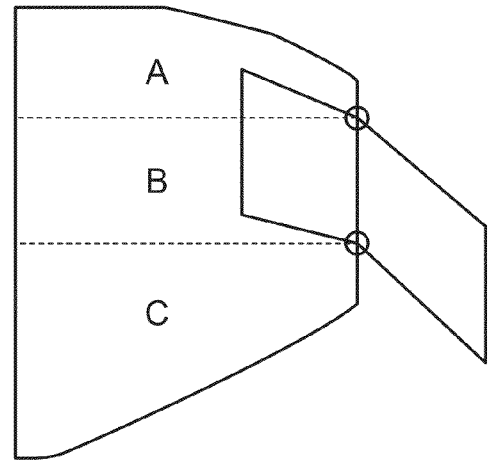
Figure 7C:
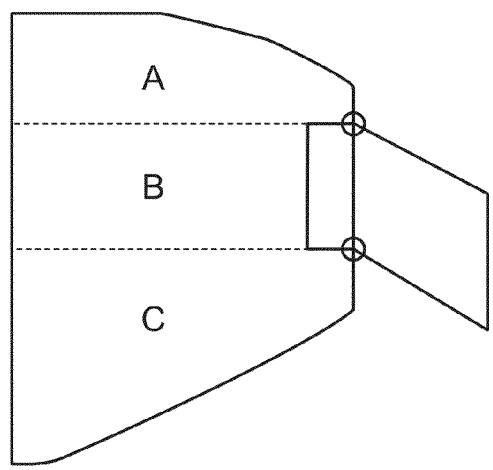

As described above, the fastening system may comprise an elastic/stretch member (ear). Referring to FIGS. 7A, 7B, and 7C, the elastic/stretch member (ear) may be divided into 3 Ear Zones, characterized by a closure member's (tab) position when attached to the elastic/stretch member (ear). Ear Zones A, B and C are demarked by the attachment of the closure member (tab) to the elastic/stretch member (ear), namely by two horizontal lines drawn at the upper and lower points of intersection between the elastic/stretch member (ear) and a closure member (tab) when attached to each other. Ear Zone A is defined as the portion of the elastic/stretch member (ear) that lies above the horizontal line drawn at the upper point of intersection between the elastic/stretch member (ear) and a closure member (tab). Ear Zone B is defined as the portion of the elastic/stretch member (ear) that lies between the horizontal line drawn at the upper point of intersection between the elastic/stretch member (ear) and a closure member (tab) and the horizontal line drawn at the lower point of intersection between the elastic/stretch member (ear) and a closure member (tab). Ear Zone C is defined as the portion of the elastic/stretch member (ear) that lies below the horizontal line drawn at the lower point of intersection between the elastic/stretch member (ear) and a closure member (tab). The Ear Zones are parallel to each other and the common borders of Ear Zones A and B, and the common borders of Ear Zones B and C, respectively, are straight lines.

The width of the elastic/stretch member (ear) is typically from 40 to 80 mm, preferably from 45 to 75 mm, more preferably 45 to 55 mm. The height of the elastic/stretch member (ear) is typically from 40 to 130 mm, preferably from 45 to 120 mm, more preferably 80 to 100 mm.

Figure 9A:
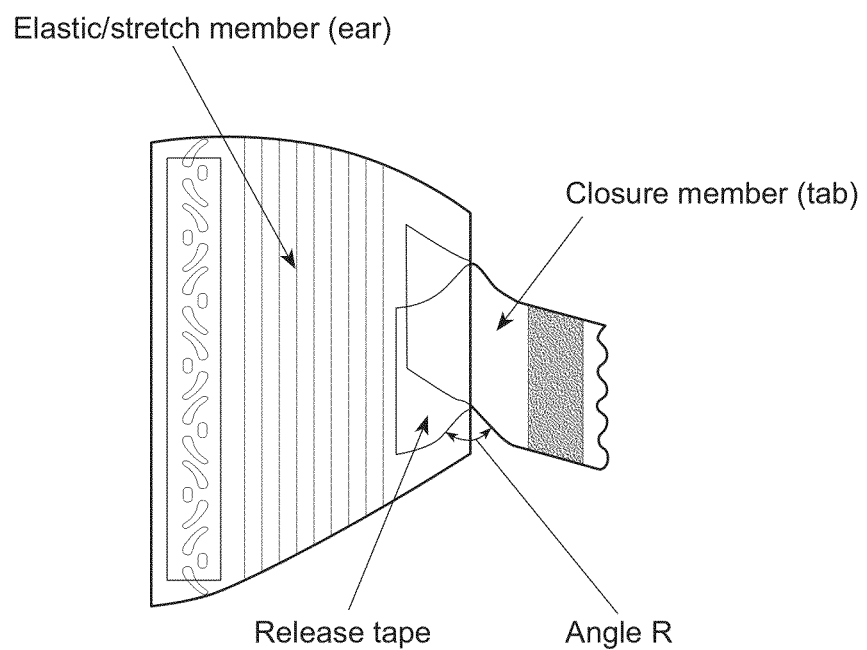
Figure 9B:
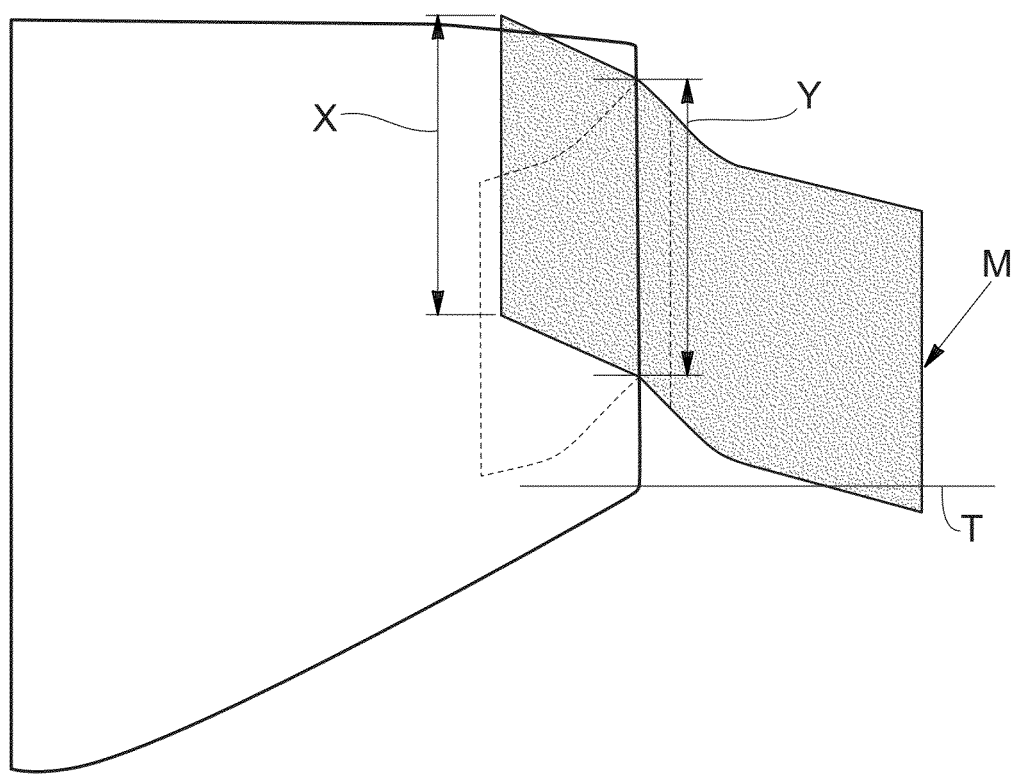

Applicants have also found that the vertical placement of the closure member (tab) when attached to the elastic/stretch member (ear) may affect the directing of force when the closure member (tab) is attached to a landing member. Referring to FIG. 9B, the midpoint (M) of the distal portion of the closure member (tab), i.e. the end not attached to the elastic/stretch member, is identified. Also marked is a horizontal line drawn through the point where the distal edge of the elastic/stretch member (ear), i.e. the end not attached to the waist region of the absorbent article, transitions into the lower edge of the elastic/stretch member (ear). In some preferred embodiments, the midpoint M is above (in the machine direction) horizontal line T. Applicants have also found that the height of the closure member (tab) at its inboard edge, relative to its height in Tab Zone B may affect the directing of force when the closure member (tab) is attached to a landing member. As depicted in FIG. 9B, the height at the inboard edge is shown as x, and the height in Tab Zone B is shown as y. In some embodiments, y is measured as the height in Tab Zone B at the outboard edge of the elastic/stretch member (ear). In some embodiments, y is measured as the height in Tab Zone B at the midpoint (in the cross-direction) of Tab Zone B. In some embodiments, y is measured as the average height in Tab Zone B. Preferably, in some embodiments, x is greater than or equal to y, more preferably x is greater than y.

Figure 8A:
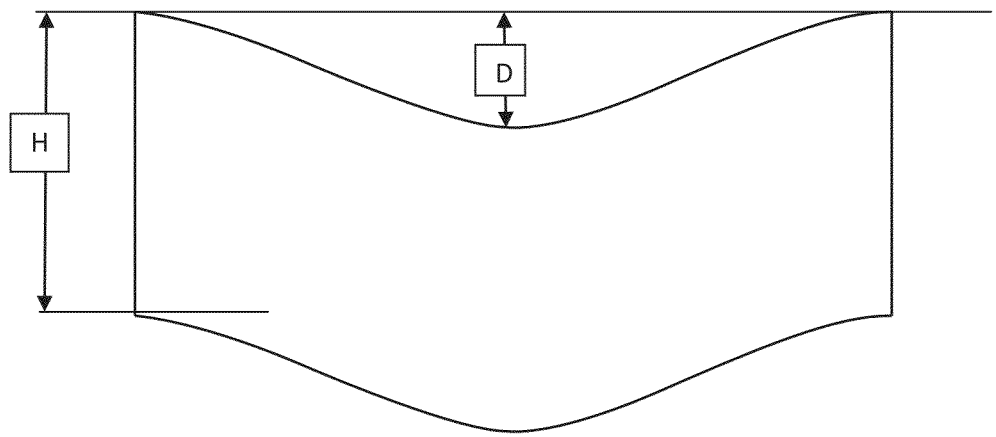
FIG. 8A is a plan view of a non-rectangular landing member, showing a dip near its centerline.

As described above, the fastening system may comprise a landing member adapted to releasably engage the closure member (tab). Applicants have found that the closure members (tabs) of the present invention may advantageously be combined with a non-rectangular landing member. Referring to FIG. 8A, the shape of the non-rectangular landing member is characterized by the center or medial portion of the landing member dipping below a horizontal line drawn between the upper ends of the outer edges of the landing member. The depth of the dip (D) is typically from 10 to 30 mm, preferably from 10 to 20 mm. In some embodiments, the depth of the dip is measured as a function of the height (H) of the landing member, where e.g., the ratio of D to H is from 1:3 to 1:4, when measured at the lateral midpoint of the landing member. In some embodiments, the landing member may be a component attached to the topsheet of an absorbent article, or it may be an area integral to the topsheet of an absorbent article.

Figure 8B:
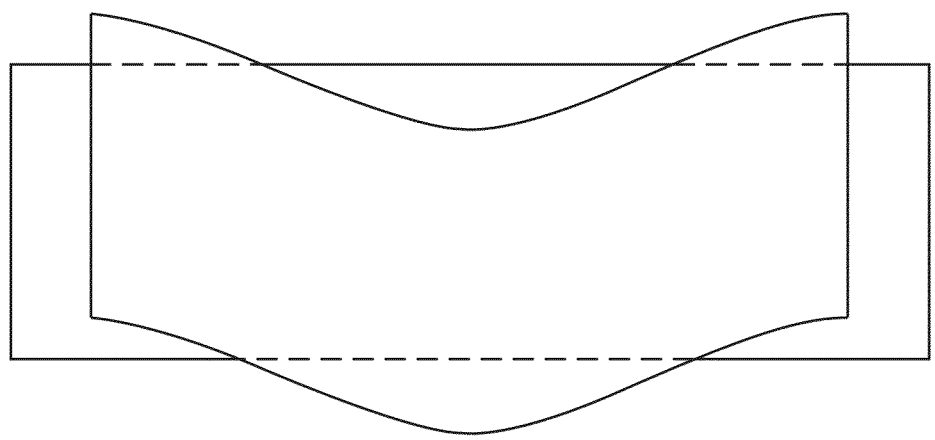
FIG. 8B is a plan view of a non-rectangular graphic printed over a rectangular landing member.

In another embodiment, the non-rectangular landing member may advantageously be formed by providing indicia, e.g. printed graphics, superimposed onto a rectangular landing member, as shown in FIG. 8B. By marking the area where a non-rectangular landing member is perceived to be, superimposed onto an area where a rectangular landing member actually is, it may assist a caregiver in locating an area for attaching the closure member (tab) to the area to secure the absorbent article by engaging the complimentary portions of the fastening system, that would avail the benefits of having provided an actual non-rectangular landing member. An added benefit associated with such an embodiment is reduced cost. For example, there is some cost associated with changing a manufacturing line that assembles absorbent article components into absorbent articles where a rectangular landing member is used to a line where a non-rectangular landing member is used. If the cost of providing indicia, e.g. printing a graphic, that appears as a non-rectangular landing member is less than the aforementioned cost, then this would result in savings.

As described above, the fastening system may comprise a release tape that protects the fastening elements, e.g. hooks, of the closure member (tab) from insult prior to use. Applicants have found that the closure members (tabs) of the present invention may advantageously be combined with a release tape that is dimensioned to substantially mirror the image of the closure member (tab) about an axis defined by the lateral edge of the elastic/stretch member, as shown in FIGS. 9A to 9D. When used in combination with a release tape, the function of the portion of the closure member (tab) located within Tab Zone B further includes enabling an increase in the angle (Angle R) formed between the release tape and fastening tape sandwich when unfolded, preferably at least 90°, to prevent or minimize tearing or zippering when a load is applied during use for closure. In some embodiments, Angle R does not exceed 120°, preferably being from about 100° to about 120°. As is shown in FIGS. 9C and 9D, the widening of Angle R substantially reduces the presence of a point or peak upon the axis upon which the distal end of the elastic/stretch member falls. Thus, in some embodiments, Angle R may be from 90° to 180°, preferably from 120° to 180°, and in other embodiments 180°. For example, in FIG. 9D, Angle R is widened to 180°.

Figure 9E:
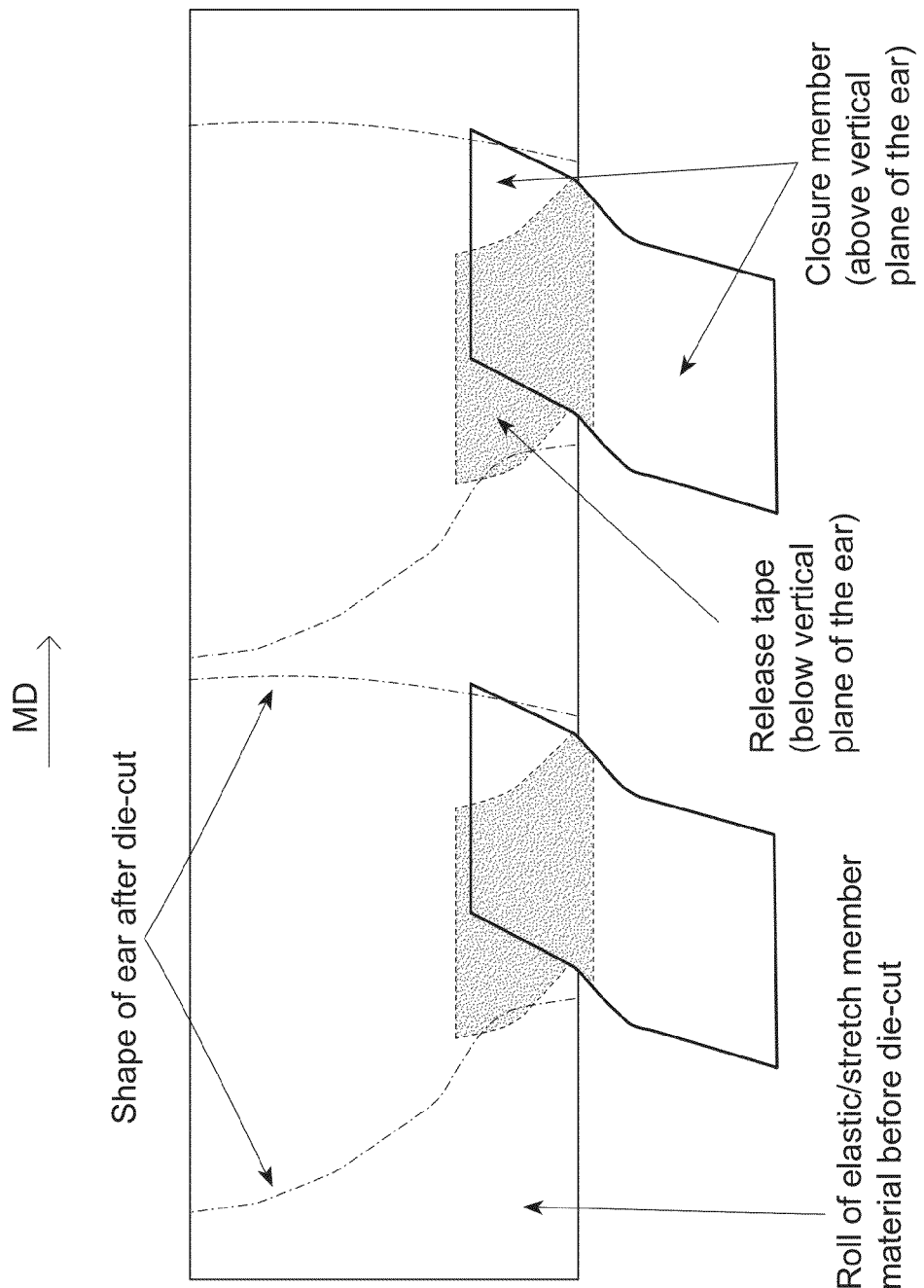
FIG. 9E is an overhead view of a fastening system comprising an elastic/stretch member (ear) with a closure member (tab) and a release tape during its manufacture on an assembly line.

Applicants have also found that improved force distribution may be achieved when the closure member (tab), the release tape, or both the closure member (tab) and the release tape are configured such that they (independently) form a continuous shape with the upper edge (in the case of the closure member (tab)) or the lower edge (in the case of the release tape), of the elastic/stretch member (ear). This may be embodied in three ways: (a) only the release tape forms a continuous shape with the lower edge of the elastic/stretch member (ear), (not shown); or preferably, (b) only the closure member (tab) forms a continuous shape with the upper edge of the elastic/stretch member (ear), as shown in FIG. 9B; or more preferably, (c) the closure member (tab) forms a continuous shape with the upper edge of the elastic/stretch member (ear), and the release tape forms a continuous shape with the lower edge of the elastic/stretch member (ear), as shown in FIG. 9E.

Figure 9F:
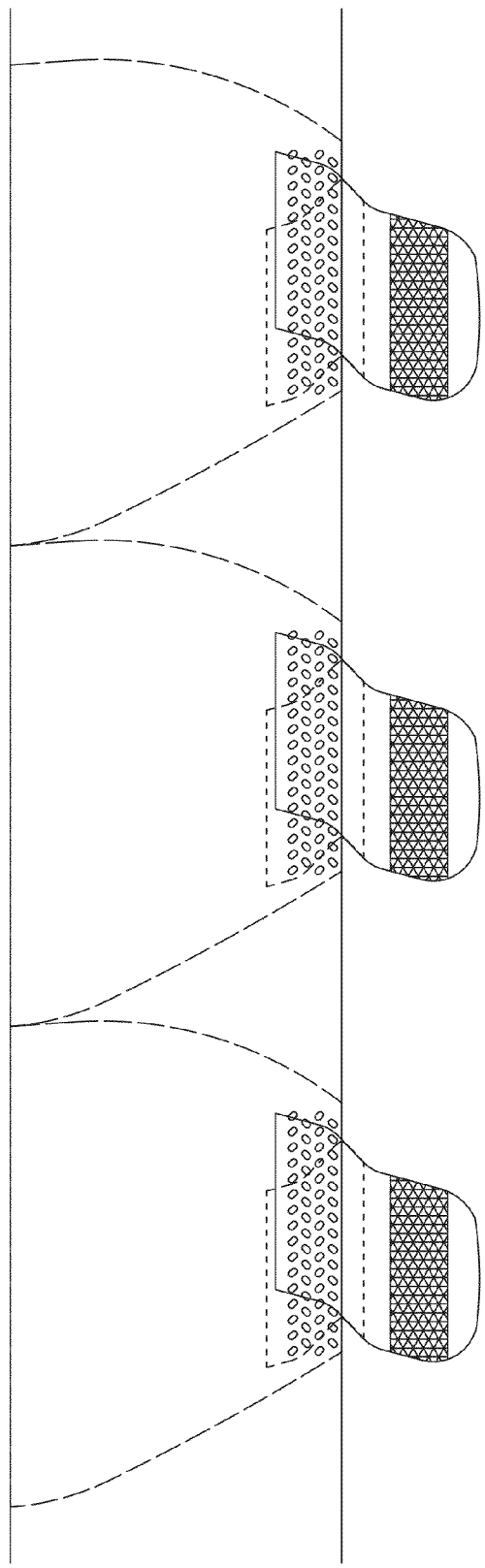
FIGS. 9F, 9G, and 9H are plan views of a fastening system comprising an elastic/stretch member (ear) with a closure member (tab).
Figure 9G:
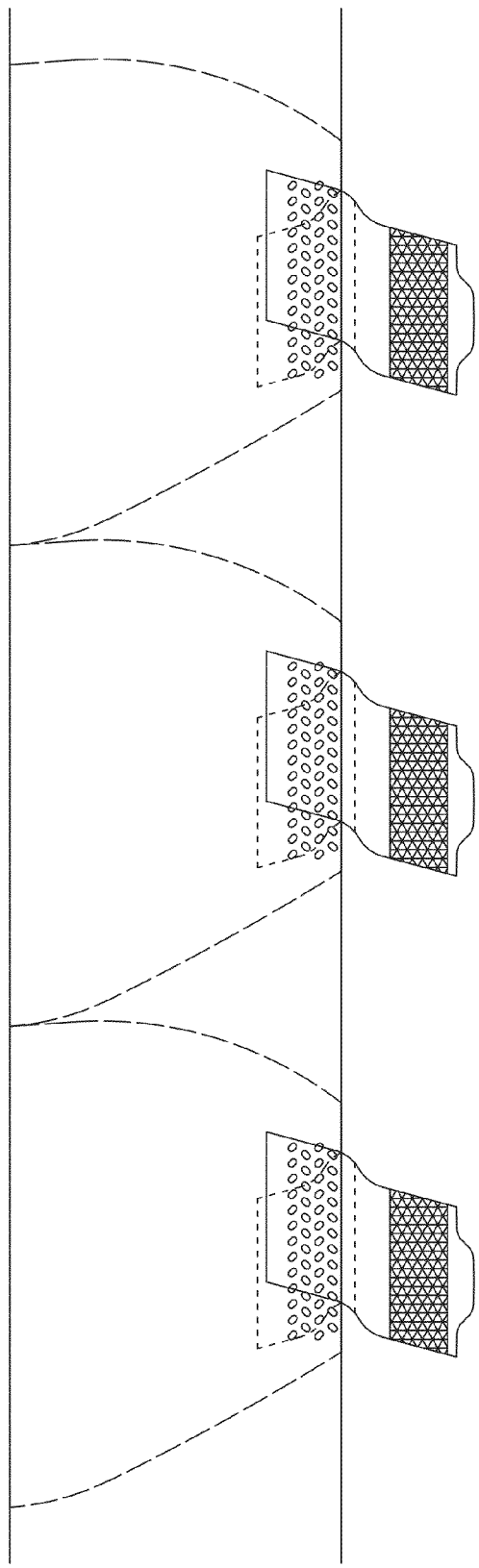

In another embodiment, neither the closure member (tab), nor the release tape are configured such that they (independently) form a continuous shape with the upper edge (in the case of the closure member (tab)) or the lower edge (in the case of the release tape), of the elastic/stretch member (ear), as shown in each of FIGS. 9F and 9G.

Figure 9H:
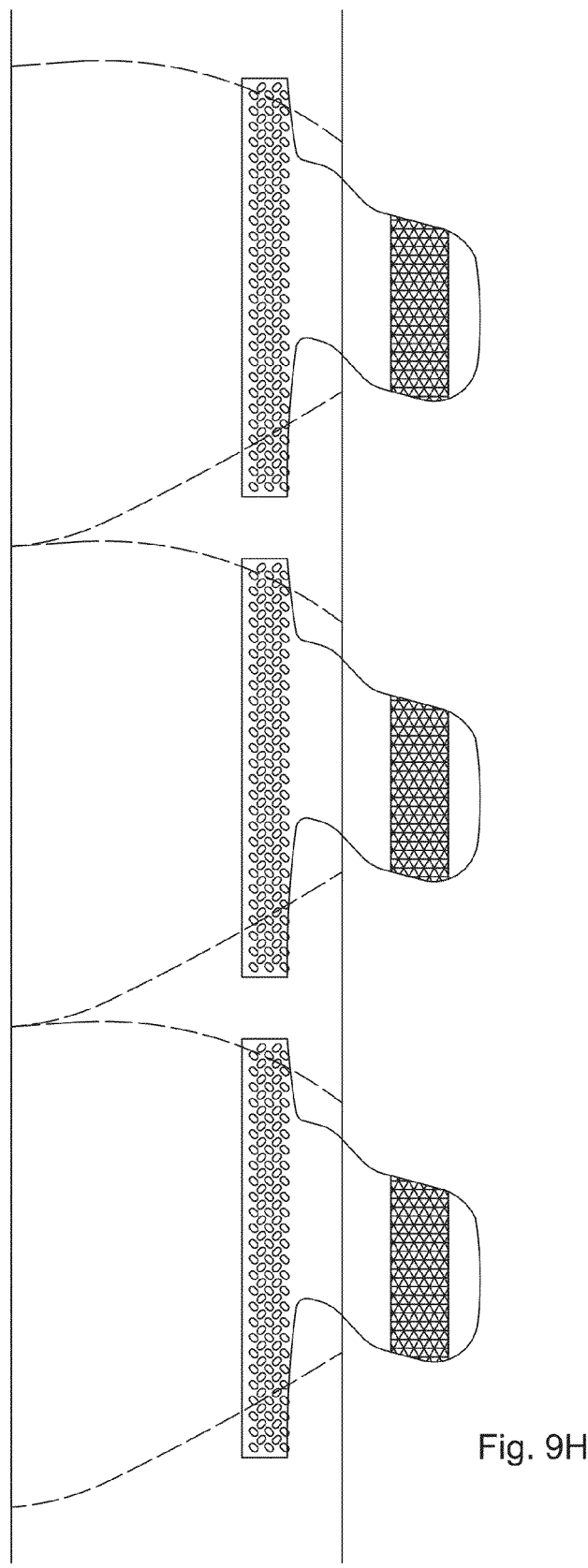
Figure 10:
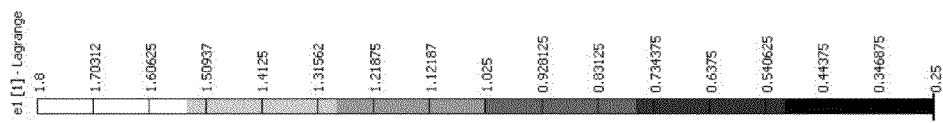
FIG. 10 is a plot showing the amount of force being applied to a fastening system test sample, using strain mapping technique.
Figure 10:
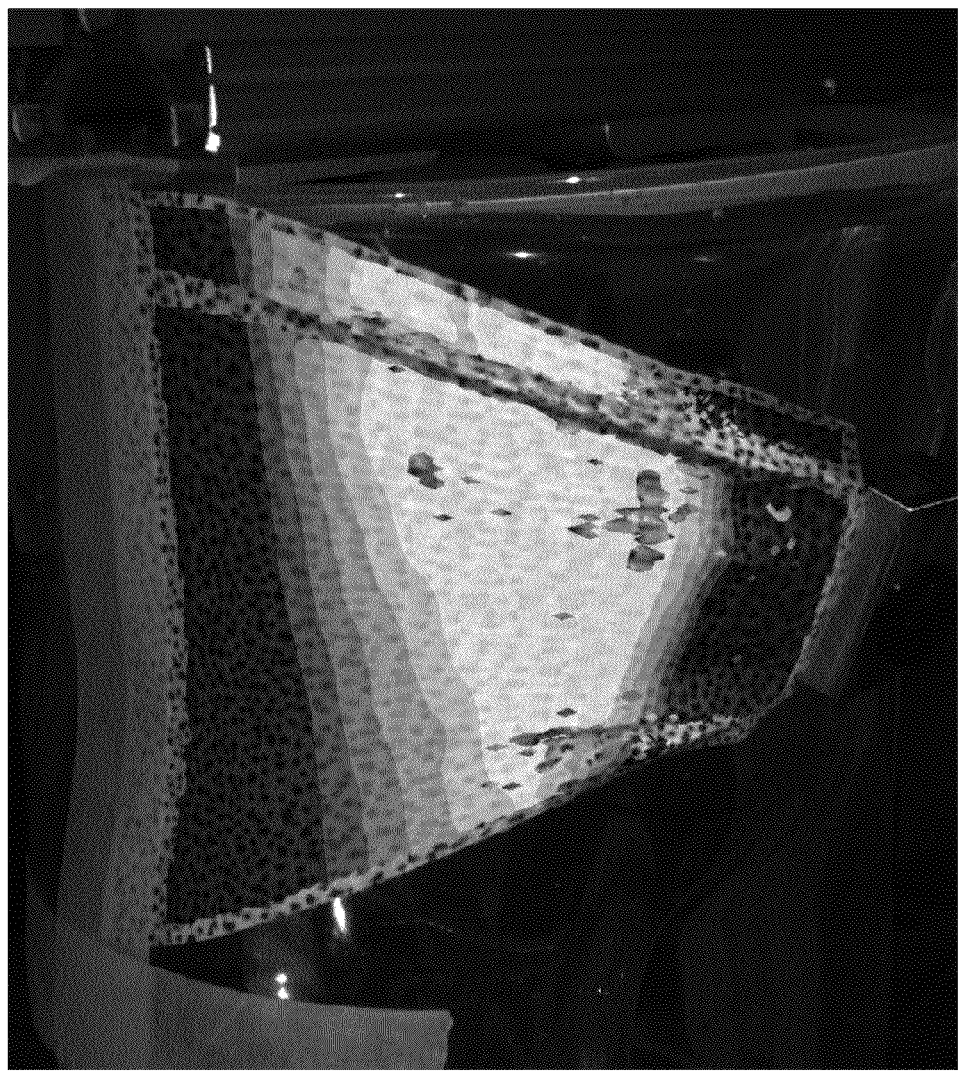
Figure 11:
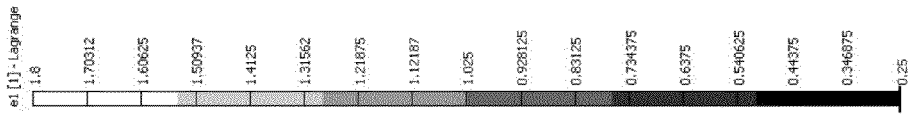
FIG. 11 is a plot showing the amount of force being applied to a fastening system test sample, using strain mapping technique.
Figure 11:
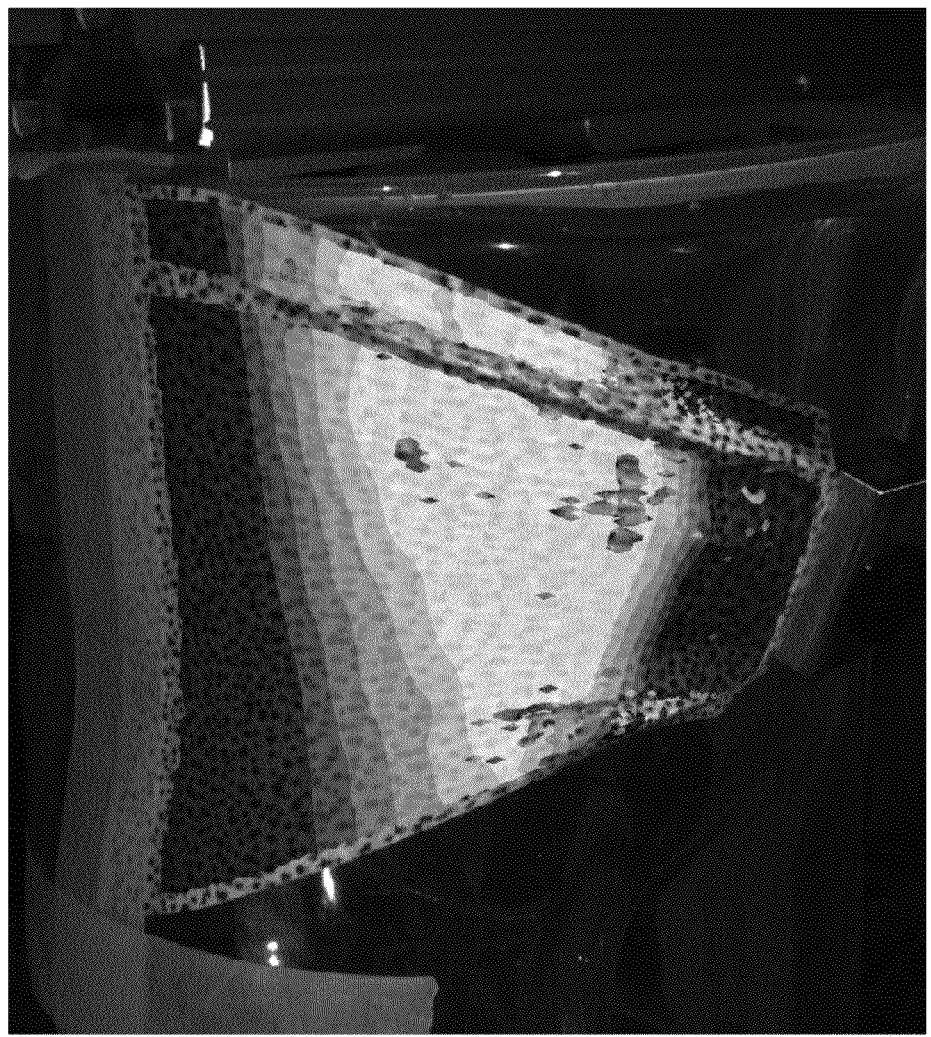
Figure 12:
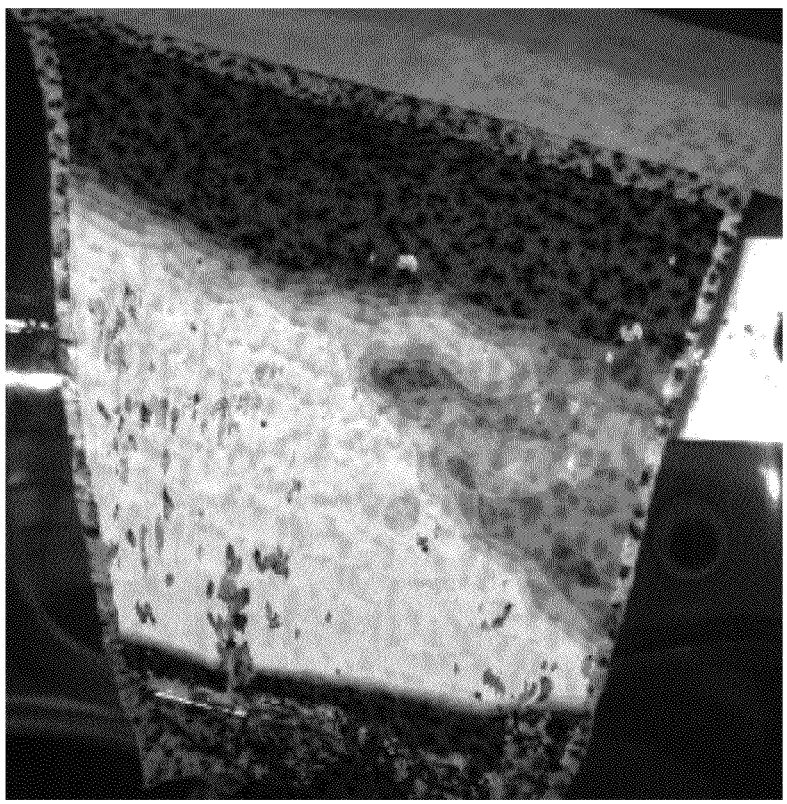
FIG. 12 is a plot showing the amount of force being applied to a fastening system test sample, using strain mapping technique.
Figure 12:
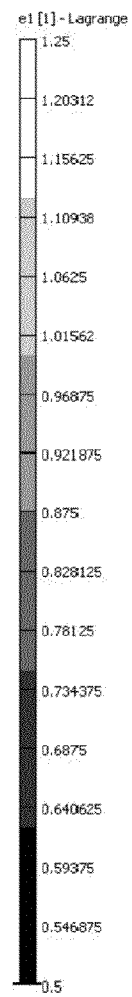
Figure 13:
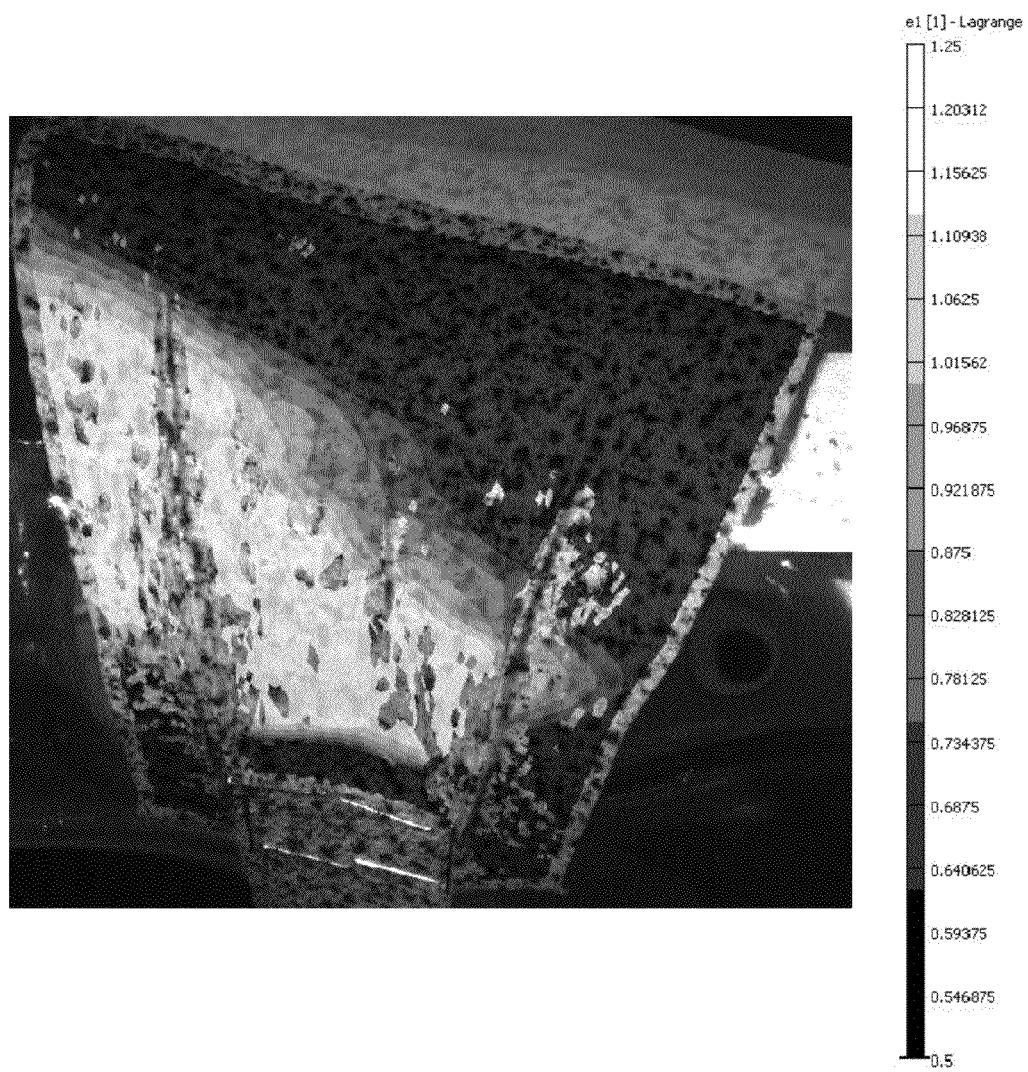
FIG. 13 is a plot showing the amount of force being applied to a fastening system test sample, using strain mapping technique.

In a preferred embodiment, the closure member (tab) is configured with extended portions at the inboard edge of the member, such that the closure member (tab) forms a continuous shape with the upper edge of the elastic/stretch member (ear), and it forms a continuous shape with the lower edge of the elastic/stretch member (ear), as shown in FIG. 9H.

Referring back to FIG. 9E, a typical manufacturing process is illustrated, where a roll of elastic/stretch member material moves in the MD, and the release tape/closure member (tab) sandwich is splayed so that the release tape portion of the sandwich is disposed below the vertical plane of the elastic/stretch member material and the closure member (tab) portion of the sandwich is disposed above such vertical plane, and then the shape of the elastic/stretch member (ear) is die-cut, causing the closure member (tab) or release tape, to take on the same shape as the upper or lower edge of the elastic/stretch member (ear), respectively.

Applicants have found that fastening systems according to the invention provide for directing direct forces developed during closure by the elastic/stretch member (ear) in a predetermined manner or location. For example, it is preferable to direct forces from the elastic/stretch member (ear) and closure system (tab) into the chassis of the absorbent article in such a manner that force at the upper waist regions of the absorbent article that correspond with a region on the wearer at or above the iliac crest provide better fit. Without wishing to be bound by theory, Applicants believe this is a targeted area on the wearer's body for friction lock of the absorbent article. This fit is better achieved by directing force at the top of the elastic/stretch member (ear) which is attached to the waist region of the absorbent article. Contrastingly, existing designs of the elastic/stretch member (ear) and attachment of the high modulus closure member (tab) do not adequately direct force, but instead concentrate force along the centerline of the attachment of the two members, which imparts a force into the absorbent article chassis that is below the iliac crest, which may cause sagging and slippage during use.

Without wishing to be bound by theory, Applicants believe that to maintain fit of the absorbent article over time by friction locking at or above the iliac crest of the wearer, that there is a significant area of higher strain (and thus higher force) in Ear Zone A, which is similar to or somewhat higher than Ear Zone B. Preferably, Ear Zone A has larger area of high force than Ear Zone C, so as to reduce red-marking or discomfort in the upper leg area. The fastening systems according to the invention may be characterized by the amount of strain in Ear Zone A, when the closure member (tab) is attached to an elastic/stretch member (ear) and a load is applied to the end of the closure member (tab) not connected to the elastic/stretch member, to cause the elastic/stretch member (ear) to experience 100% strain. A suitable test method is described in the Examples section below. In some embodiments, the percent strain of the elastic/stretch member (ear) measured at 100% strain of the elastic/stretch member, is such that at least 40% of Ear Zone A is at 75% strain or greater, preferably at least 60% of Ear Zone A is at 75% strain or greater, more preferably at least 70% of Ear Zone A is at 75% strain or greater. In some embodiments, the percent strain of the elastic/stretch member (ear) measured at 100% strain of the elastic/stretch member, is such that at least 50% of Ear Zone A is at 50% strain or greater, preferably at least 50% of Ear Zone A is at 60% strain or greater, more preferably at least 50% of Ear Zone A is at 75% strain or greater. In some embodiments, the percent strain of the elastic/stretch member (ear) measured at 100% strain of the elastic/stretch member, is such that at least 75% of Ear Zone A is at 50% strain or greater, preferably at least 60% of Ear Zone A is at 70% strain or greater, more preferably at least 45% of Ear Zone A is at 90% strain or greater. In some embodiments, the percent strain for the given area of Ear Zone A described above, will not exceed 100%.

Furthermore, Applicants have found that fastening systems according to the invention may achieve additional benefits, including: (a) providing a less expensive way to get maximum length of bond of the closure member (tab) and elastic/stretch member (ear) when done in a tape sandwich manner (e.g. fastening tape and release tape splay); and (b) creating a wider force band into the elastic/stretch member (ear) from the closure member (tab) and the wider the force band the better the fit and the more comfortable the fit.

Still further, Applicants have found that when the closure member (tab) of the invention is combined with the shaped landing member (as discussed above), the ability to further distribute force to the upper most region of the stretch/elastic member is further enhanced resulting in better sustained fit compared to use of the inventive closure member (tab) alone. Without wishing to be bound by theory, Applicants believe that the effect of the shaped landing member guides the application of the closure member (tab) in a downward angle which further increases force in the upper region of the stretch/elastic member.

EXAMPLES

The following examples may be useful in understanding the present disclosure.

The plots shown in FIGS. 10 to 13, show results from strain mapping of elastic/stretch members (ears) to which various closure members (tabs) had been fastened. In the plots shown in FIGS. 10 and 12, closure members (tabs) according to the invention were used. In the plots shown in FIGS. 11 and 13, closure members (tabs) according to the prior art were used. The scale shown represents percent strain of the elastic/stretch member (ear) where, e.g., 0.25 represents 25% strain, and 1.80 represents 180% strain. Strain was measured and the plots were generated using Vic-3D 2009 software (ver. 2009.1.o474MS) using, commercially available software (Correlated Solutions, Inc., Columbia, S.C.) that applies Digital Image Correlation, and 2 Photron SA3 high speed video cameras. Digital Image Correlation is an optical method used to measure deformation on an object surface. The method tracks the gray-scale value pattern in small neighborhoods called subsets (defined subportions of the total surface area being measured) during deformation. Using this method, actual object movement is measured and the Lagrangian strain tensor is available at every point on the specimen's surface.

The exemplary samples are fastening systems that have a closure member (tab) fastened to an elastic/stretch member (ear). Each sample was constructed using the following materials, the difference between the samples being their shape. The closure member (tab) is a 3 layer composite web, in which a 50 gsm spunbonded nonwoven is adhered to a 28 gsm film, using a 25 gsm adhesive. The elastic/stretch member (ear) is a 5 layer composite web, in which a 27 gsm polypropylene carded nonwoven is adhered to a 54.5 gsm elastomeric film using a 15.5 gsm adhesive, which in turn is adhered to a 17 gsm polypropylene SMS nonwoven using a 15.5 gsm adhesive. Each closure member (tab) was fastened to an elastic/stretch member (ear). Once constructed, each sample was subjected to a tensile test, where a load is applied to the sample to force it to strain. To simulate customary use of the fastening systems with an absorbent article, the samples were tested over a curved surface, where the fastening system was draped over a mannequin of a child's hip and the end of the elastic/stretch member (ear) that would be adhered to the waist band of an absorbent article was secured to the mannequin on one side of the mannequin. The fastening system was draped over the mannequin and the end of the closure member (tab) that would be adhered to the complimentary waist band of an absorbent article, e.g. at the landing member was attached to an 850 g weight, and then the tensile test was performed. Measurement of strain ("strain mapping") is conducted during the test. The technique of strain mapping, may be carried out according to the following procedure:

(1) Preparing the sample—The sample is placed flat on a piece of cardboard that exceeds its area, and taped in place to hold it flat. Using an Ultra fine tip permanent marker, dots are randomly placed across the entire surface of the sample in a very dense pattern.
(2) Running the test—Two calibrated high speed video cameras are focused on the sample with the complete test area within the field of view. The cameras are turned on to continuously capture video image data while the sample is pulled in tension according to the tensile test. At the conclusion of the test, the images are saved on a computer that controls the cameras, and post processed in Vic 3D image processing software.
(3) Plotting the result—Using VIC-3D software, both sets of camera data are used to process the strain maps. Within the software there are several settings that allow the operator to look at various data types. Here, major principle strain was selected for the 2D plot. The maximum and minimum strain ranges are manipulated to optimize resolution for the area of strain being measured.

Sample A is a fastening system having a closure member (tab) according to the invention. Sample B is a fastening system having a closure member (tab) according to the prior art, and bearing a bearing a straight/rectangular shape slightly angled position. Sample C is a fastening system having a closure member (tab) according to the invention. Sample D is a fastening system having a closure member (tab) according to the prior art, and bearing a straight/rectangular shape with a lateral position.

The plots of each of samples A (FIG. 10) and C (FIG. 12) show higher amounts of force being imparted into the elastic/stretch member (ear) than each of Samples B (FIG. 11) and D (FIG. 13), respectively. This demonstrates that samples according to the invention provide for a significant amount of force in the top region of the elastic/stretch member (ear) versus those of the prior art. As discussed above, this force is believed to be subsequently directed to the upper portion of the back waist region of an absorbent article, which improves fit during wear by friction helping to hold the absorbent article at or above the iliac crest of the wearer.

Sample E is a fastening system having a closure member (tab) according to the invention, combined with a landing member according to the invention. Sample F is a fastening system having a closure member (tab) according to the invention combined with a landing member according to the prior art, such landing member bearing a rectangular shape. The closure member (tab) components of Samples E and F were constructed using the same materials as the samples above. The landing member component of Samples E and F were constructed using the following materials, the difference between the samples being their shape. The landing member is an extrusion laminate of a 28 gsm carded, polypropylene fiber nonwoven and a 33 gsm film.

Figure 14:
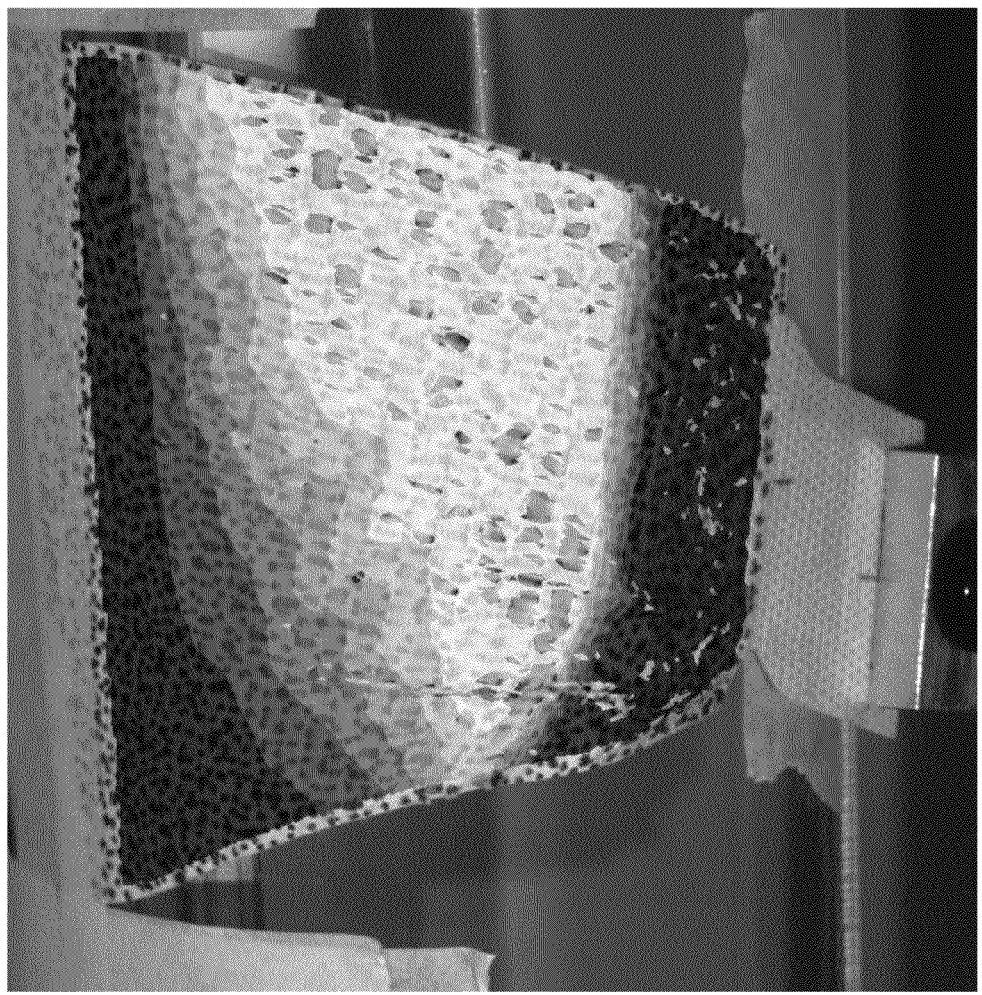
FIG. 14 is a plot showing the amount of force being applied to a fastening system test sample, using strain mapping technique.
Figure 15:
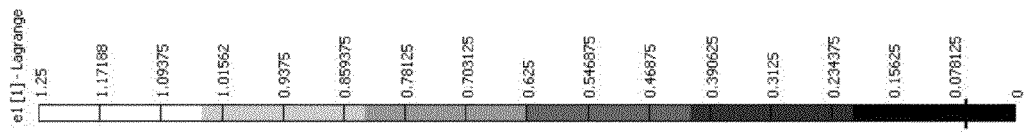
FIG. 15 is a plot showing the amount of force being applied to a fastening system test sample, using strain mapping technique.
Figure 15:
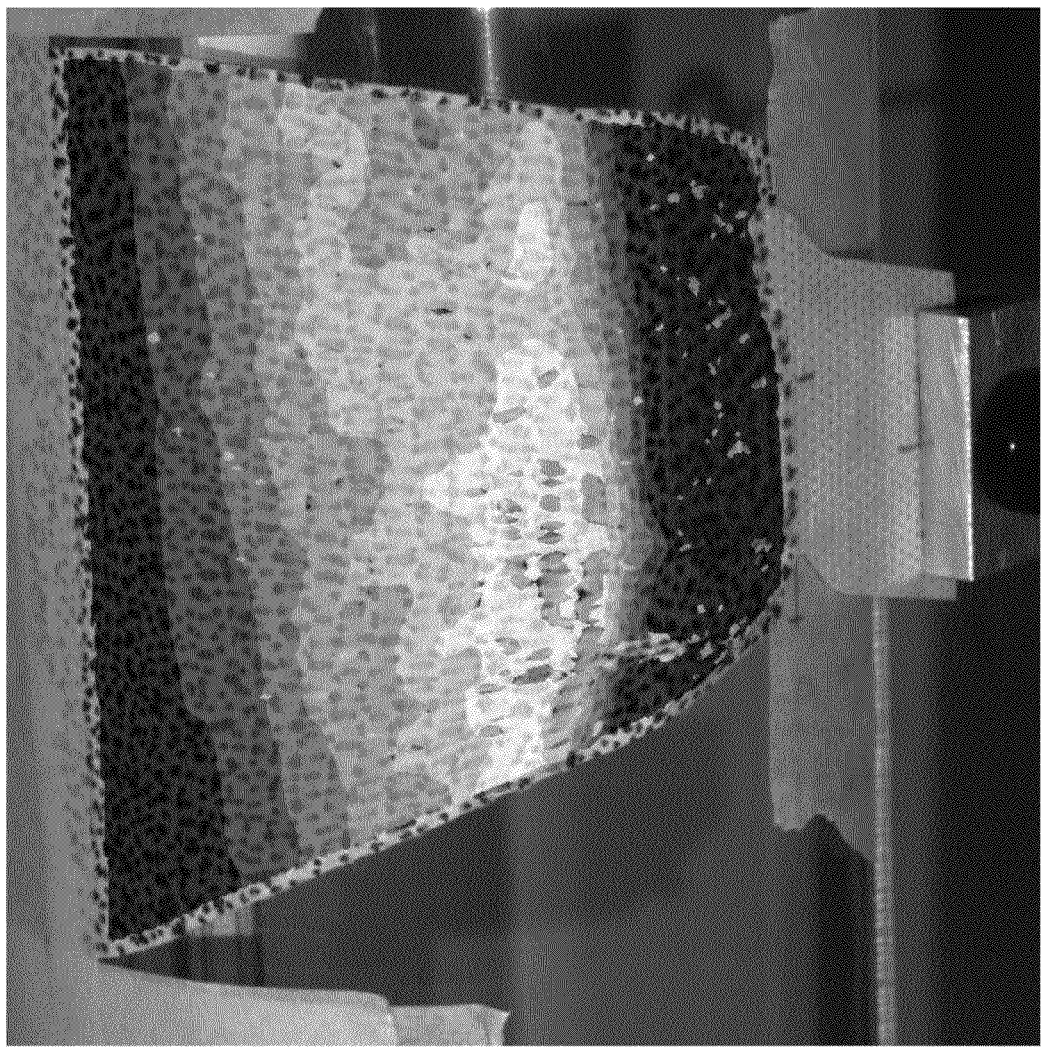

The plot of each of Sample E (FIG. 14) shows higher amounts of force being imparted into the elastic/stretch member (ear) than Samples F (FIG. 15). This demonstrates that the sample combining a closure member (tab) according to the invention with a landing member according to the invention provides for a significant amount of force in the top region of the elastic/stretch member (ear) versus combining a closure member (tab) according to the invention with a landing member of the prior art. As discussed above, this force is believed to be subsequently directed to the upper portion of the back waist region of an absorbent article, which improves fit during wear by friction helping to hold the absorbent article at or above the iliac crest of the wearer.

Sample G is a fastening system having a closure member (tab) according to the invention, combined with a release tape according to the invention. The closure member (tab) component of Sample G was constructed using the same materials as the samples above. The release tape component of Sample G was constructed using a 28 gsm film, where the closure member (tab) and the release tape were configured such that they (independently) form a continuous shape with the upper edge (in the case of the closure member (tab)) or the lower edge (in the case of the release tape).

Figure 16:
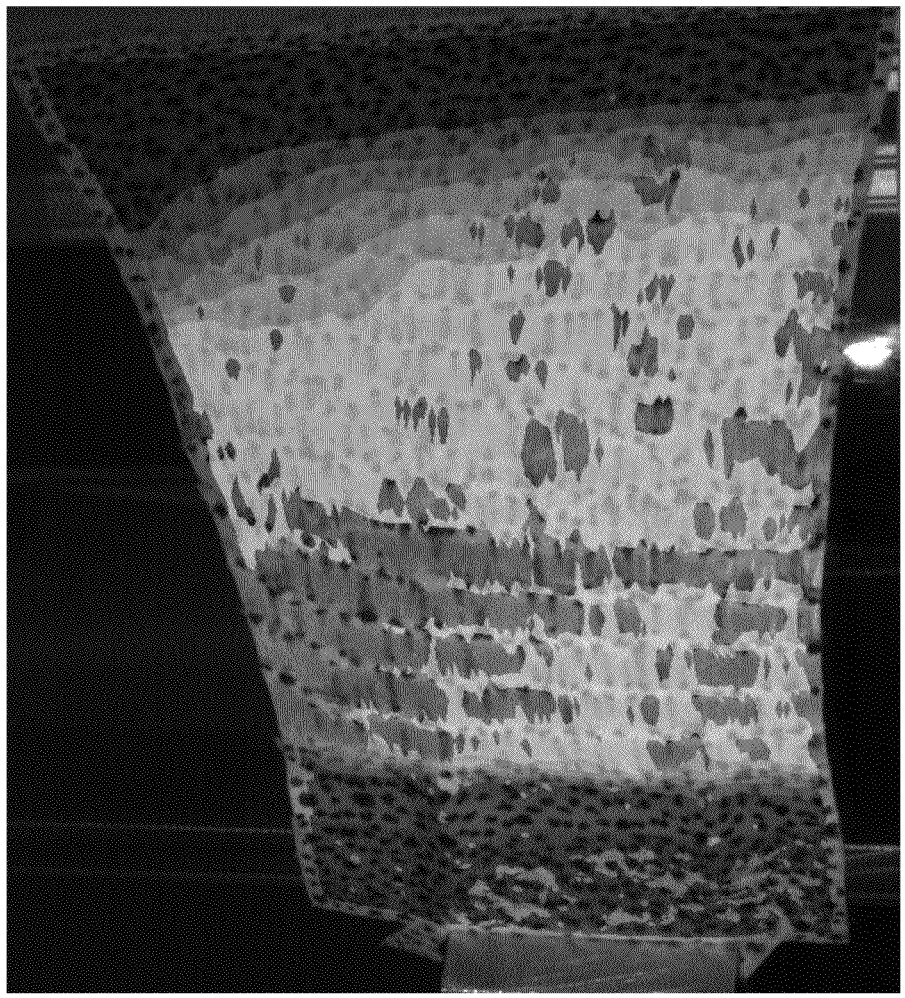
FIG. 16 is a plot showing the amount of force being applied to a fastening system test sample, using strain mapping technique.

The plot of Sample G (FIG. 16) shows high amounts of force being imparted into the elastic/stretch member. This demonstrates that the sample combining a closure member (tab) according to the invention with a release tape according to the invention provides for a significant amount of force in the top region of the elastic/stretch member (ear). As discussed above, this force is believed to be subsequently directed to the upper portion of the back waist region of an absorbent article, which improves fit during wear by friction helping to hold the absorbent article at or above the iliac crest of the wearer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fastening system comprising a closure member and a stretch member:
   (a) wherein the closure member is divided into Tab Zones characterized as follows:
      i. Tab Zone A is defined as the portion of the closure member that is not attached to nor lying in the same vertical plane, when the member is laid flat in horizontal position, as viewed from above, as the stretch member, less the portion of Tab Zone B;
      ii. Tab Zone C is defined as the portion of the closure member that is attached to and lies in the same vertical plane, when the member is laid flat in horizontal position, as viewed from above, as the stretch member, less the portion of Tab Zone B;
      iii. Tab Zone B occupies the transitional area between Tab Zone A and Tab Zone C, and is defined as a portion of the closure member which includes both a sub-portion that is not attached to nor lying in the same vertical plane, when the member is laid flat in horizontal position, as viewed from above, as the stretch member and a sub-portion that is attached to and lies in the same vertical plane as the stretch member; and
      iv. wherein the Tab Zones are parallel to each other and their lateral borders are straight lines;
   (b) wherein the stretch member is divided into Ear Zones characterized as follows:
      i. Ear Zone A is defined as the portion of the stretch member that lies above the horizontal line drawn at the upper point of intersection between the stretch member and the closure member;
      ii. Ear Zone B is defined as the portion of the stretch member that lies between the horizontal line drawn at the upper point of intersection between the stretch member and a closure member and the horizontal line drawn at the lower point of intersection between the stretch member and the closure member;
      iii. Ear Zone C is defined as the portion of the stretch member that lies below the horizontal line drawn at the lower point of intersection between the stretch member and the closure member; and
      iv. wherein the Ear Zones are parallel to each other and the common borders of Ear Zones A and B, and the common borders of Ear Zones B and C, respectively, are straight lines;
   (c) wherein the angle at which the closure member travels through each of the Tab Zones is characterized by the closure member's position when attached to the stretch member, as follows:
      i. Tab Angle A is defined as the angle between: (i) a line drawn from the point at which one edge of the closure member intersects the common border of Tab Zones A and B, and the point at which the same edge of the closure member intersects the other border of Tab Zone A; and (ii) a line drawn upon such other border of Tab Zone A;
      ii. Tab Angle B is defined as the angle between: (i) a line drawn from the point at which one edge of the closure member intersects the common border of Tab Zones A and B, and the point at which the same edge of the closure member intersects the common border of Tab Zones B and C; and (ii) a line drawn upon the common border of Tab Zones A and B;
      iii. Tab Angle C is defined as the angle between: (i) a line drawn from the point at which one edge of the closure member intersects the common border of Tab Zones B and C, and the point at which the same edge of the closure member intersects the other border of Tab Zone C; and (ii) a line drawn upon the common border of Tab Zones B and C; and
   wherein Angle A is not equal to or substantially similar to Angle B, and/or, Angle B is not equal to or substantially similar to Angle C; and
   wherein Angle B is greater than Angle A, and Angle A is greater than Angle C.

2. The fastening system according to claim 1, wherein Angle B is greater than Angle A by about 10° or more.

3. The fastening system according to claim 1, wherein Angle B is greater than Angle C by about 10° or more.

4. The fastening system according to claim 1, wherein each of Angles A, B, and C, independently, is from about 45 to about 75°.

5. The fastening system according to claim 4, wherein each of Angles A and B, independently, is from about 55 to about 75°.

6. The fastening system according to claim 1, wherein the width of Tab Zone A is from about 20 to about 35 mm.

7. The fastening system according to claim 6, wherein the width of Tab Zone A is from about 20 to about 25 mm.

8. The fastening system according to claim 1, wherein the width of Tab Zone B is from about 5 to about 20 mm.

9. The fastening system according to claim 8, wherein the width of Tab Zone B is from about 5 to about 15 mm.

10. The fastening system according to claim 1, wherein the width of Tab Zone B is symmetrically distributed relative to the edge of the stretch member distal to the stretch member's attachment to the waist region of an absorbent article.

11. The fastening system according to claim 1, wherein the length of each Tab Zone is from about 28 to about 40 mm.

12. The fastening system according to claim 1, wherein the midpoint (M) of the distal portion of the closure member is above the horizontal line drawn through the point where the distal edge of the stretch member transitions into the lower edge of the stretch member.

13. The fastening system according to claim 1, further comprising a release tape which is dimensioned to substantially mirror the image of the closure member about an axis defined by the lateral edge of the stretch member, forming an angle (Angle R) between the release tape and fastening tape sandwich when unfolded of at least about 90°.

14. The fastening system according to claim 13, wherein Angle R is from about 100° to about 120°.

15. The fastening system according to claim 13, wherein Angle R is from about 120° to about 180°.

16. The fastening system according to claim 15, wherein Angle R is about 180°.

17. The fastening system according to claim 13, wherein the release tape forms a continuous shape with the lower edge of the stretch member.

18. The fastening system according to claim 13, wherein the closure member forms a continuous shape with the upper edge of the stretch member, and the release tape forms a continuous shape with the lower edge of the stretch member.

19. The fastening system according to claim 1, wherein the percent strain of the stretch member measured at 100% strain of the stretch member, is such that at least about 40% of Ear Zone A is at about 75% strain or greater.

20. The fastening system according to claim 19, wherein the percent strain of the stretch member measured at 100% strain of the stretch member, is such that at least about 60% of Ear Zone A is at about 75% strain or greater.

21. The fastening system according to claim 20, wherein the percent strain of the stretch member measured at 100% strain of the stretch member, is such that at least about 70% of Ear Zone A is at about 75% strain or greater.

22. The fastening system according to claim 1, wherein the percent strain of the stretch member measured at 100% strain of the elastic/stretch member, is such that at least about 50% of Ear Zone A is at about 50% strain or greater.

23. The fastening system according to claim 22, wherein the percent strain of the stretch member measured at 100% strain of the stretch member, is such that at least about 50% of Ear Zone A is at about 60% strain or greater.

24. The fastening system according to claim 23, wherein the percent strain of the stretch member measured at 100% strain of the stretch member, is such that at least about 50% of Ear Zone A is at about 75% strain or greater.

25. The fastening system according to claim 1, wherein the percent strain of the stretch member measured at 100% strain of the stretch member, is such that at least 75% of Ear Zone A is at 50% strain or greater.

26. The fastening system according to claim 1, wherein the percent strain of the stretch member measured at 100% strain of the stretch member, is such that at least 60% of Ear Zone A is at 70% strain or greater.

27. The fastening system according to claim 1, wherein the percent strain of the stretch member measured at 100% strain of the stretch member, is such that at least 45% of Ear Zone A is at 90% strain or greater.

28. The fastening system according to claim 1, wherein the closure member forms a continuous shape with the upper edge of the stretch member.

29. The fastening system according to claim 1, wherein the height of the closure member at its inboard edge (x), relative to its height in Tab Zone B (y), y being measured as the height in Tab Zone B at the outboard edge of the stretch member, is such that x is greater than or equal to y.

30. The fastening system according to claim 29, wherein x is greater than y.

31. The fastening system according to claim 1, obtained by the process of:

(a) advancing a roll of stretch member material in the MD;
(b) splaying a release tape/closure member sandwich and engaging the splayed sandwich such that the release tape portion of the sandwich is disposed below the vertical plane of the elastic/stretch member material and the closure member portion of the sandwich is disposed above such vertical plane; and then
(c) die-cutting the shape of the stretch member, causing the closure member or release tape, to take on the same shape as the upper or lower edge of the stretch member, respectively;
wherein for step (b), the closure member overlaps and extends beyond the upper edge of the elastic/stretch member's profile to be die-cut in step (c), and the release tape overlaps and extends beyond the lower edge of the elastic/stretch member's profile to be die-cut in step (c).

32. An absorbent article comprising the fastening system according to claim 1.

33. The absorbent article according to claim 32, wherein the absorbent article is selected from diapers, training pants, adult incontinence undergarments, and feminine hygiene products.

34. The absorbent article according to claim 32, wherein the absorbent article is a diaper or training pant.

35. A fastening system comprising a closure member and a stretch member:

(a) wherein the closure member is divided into Tab Zones characterized as follows:
  a. Tab Zone A is defined as the portion of the closure member that is not attached to nor lying in the same vertical plane, when the member is laid flat in horizontal position, as viewed from above, as the stretch member, less the portion of Tab Zone B;
  b. Tab Zone C is defined as the portion of the closure member that is attached to and lies in the same vertical plane, when the member is laid flat in horizontal position, as viewed from above, as the stretch member, less the portion of Tab Zone B;
  c. Tab Zone B occupies the transitional area between Tab Zone A and Tab Zone C, and is defined as a portion of the closure member which includes both a sub-portion that is not attached to nor lying in the same vertical plane, when the member is laid flat in horizontal position, as viewed from above, as the stretch member and a sub-portion that is attached to and lies in the same vertical plane as the stretch member; and
  d. wherein the Tab Zones are parallel to each other and their lateral borders are straight lines;
(b) wherein the stretch member is divided into Ear Zones characterized as follows:
  a. Ear Zone A is defined as the portion of the stretch member that lies above the horizontal line drawn at the upper point of intersection between the stretch member and the closure member;
  b. Ear Zone B is defined as the portion of the stretch member that lies between the horizontal line drawn at the upper point of intersection between the stretch member and a closure member and the horizontal line drawn at the lower point of intersection between the stretch member and the closure member;
  c. Ear Zone C is defined as the portion of the stretch member that lies below the horizontal line drawn at the lower point of intersection between the stretch member and the closure member; and d. wherein the Ear Zones are parallel to each other and the common borders of Ear Zones A and B, and the common borders of Ear Zones B and C, respectively, are straight lines;

(c) wherein the angle at which the closure member travels through each of the Tab Zones is characterized by the closure member's position when attached to the stretch member, as follows:

a. Tab Angle A is defined as the angle between: (i) a line drawn from the point at which one edge of the closure member intersects the common border of Tab Zones A and B, and the point at which the same edge of the closure member intersects the other border of Tab Zone A; and (ii) a line drawn upon such other border of Tab Zone A;

b. Tab Angle B is defined as the angle between: (i) a line drawn from the point at which one edge of the closure member intersects the common border of Tab Zones A and B, and the point at which the same edge of the closure member intersects the common border of Tab Zones B and C; and (ii) a line drawn upon the common border of Tab Zones A and B;

c. Tab Angle C is defined as the angle between: (i) a line drawn from the point at which one edge of the closure member intersects the common border of Tab Zones B and C, and the point at which the same edge of the closure member intersects the other border of Tab Zone C; and (ii) a line drawn upon the common border of Tab Zones B and C; and wherein Angle A is not equal to or substantially similar to Angle B, and/or, Angle B is not equal to or substantially similar to Angle C; and wherein each of Angles A, B, and C, independently, is from about 45 to about 75°.

36. The fastening system according to claim 35, wherein: (a) Angle B is greater than Angle A; (b) Angle B is greater than Angle C; or (c) Angle B is greater than each of Angles A and C.

37. The fastening system according to claim 35, wherein Angle B is greater than Angle A by about 10° or more.

38. The fastening system according to claim 35, wherein Angle B is greater than Angle C by about 10° or more.

39. The fastening system according to claim 35, wherein each of Angles A and B, independently, is from about 55 to about 75°.

40. The fastening system according to claim 35, wherein the width of Tab Zone A is from about 20 to about 35 mm.

41. The fastening system according to claim 40, wherein the width of Tab Zone A is from about 20 to about 25 mm.

42. The fastening system according to claim 35, wherein the width of Tab Zone B is from about 5 to about 20 mm.

43. The fastening system according to claim 42, wherein the width of Tab Zone B is from about 5 to about 15 mm.

44. The fastening system according to claim 35, wherein the width of Tab Zone B is symmetrically distributed relative to the edge of the stretch member distal to the stretch member's attachment to the waist region of an absorbent article.

45. The fastening system according to claim 35, wherein the length of each Tab Zone is from about 28 to about 40 mm.

46. The fastening system according to claim 35, wherein the midpoint (M) of the distal portion of the closure member is above the horizontal line drawn through the point where the distal edge of the stretch member transitions into the lower edge of the stretch member.

47. The fastening system according to claim 35, further comprising a release tape which is dimensioned to substantially mirror the image of the closure member about an axis defined by the lateral edge of the stretch member, forming an angle (Angle R) between the release tape and fastening tape sandwich when unfolded of at least about 90°.

48. The fastening system according to claim 47, wherein Angle R is from about 100° to about 120°.

49. The fastening system according to claim 47, wherein Angle R is from about 120° to about 180°.

50. The fastening system according to claim 49, wherein Angle R is about 180°.

51. The fastening system according to claim 35, wherein the percent strain of the stretch member measured at 100% strain of the stretch member, is such that at least about 40% of Ear Zone A is at about 75% strain or greater.

52. The fastening system according to claim 51, wherein the percent strain of the stretch member measured at 100% strain of the stretch member, is such that at least about 60% of Ear Zone A is at about 75% strain or greater.

53. The fastening system according to claim 52, wherein the percent strain of the stretch member measured at 100% strain of the stretch member, is such that at least about 70% of Ear Zone A is at about 75% strain or greater.

54. The fastening system according to claim 35, wherein the percent strain of the stretch member measured at 100% strain of the stretch member, is such that at least about 50% of Ear Zone A is at about 50% strain or greater.

55. The fastening system according to claim 54, wherein the percent strain of the stretch member measured at 100% strain of the stretch member, is such that at least about 50% of Ear Zone A is at about 60% strain or greater.

56. The fastening system according to claim 55, wherein the percent strain of the stretch member measured at 100% strain of the stretch member, is such that at least about 50% of Ear Zone A is at about 75% strain or greater.

57. The fastening system according to claim 35, wherein the percent strain of the stretch member measured at 100% strain of the stretch member, is such that at least 75% of Ear Zone A is at 50% strain or greater.

58. The fastening system according to claim 35, wherein the percent strain of the stretch member measured at 100% strain of the stretch member, is such that at least 60% of Ear Zone A is at 70% strain or greater.

59. The fastening system according to claim 35, wherein the percent strain of the stretch member measured at 100% strain of the stretch member, is such that at least 45% of Ear Zone A is at 90% strain or greater.

60. The fastening system according to claim 35, wherein the closure member forms a continuous shape with the upper edge of the stretch member.

61. The fastening system according to claim 35, wherein the release tape forms a continuous shape with the lower edge of the stretch member.

62. The fastening system according to claim 35, wherein the closure member forms a continuous shape with the upper edge of the stretch member, and the release tape forms a continuous shape with the lower edge of the stretch member.

63. The fastening system according to claim 35, wherein the height of the closure member at its inboard edge (x), relative to its height in Tab Zone B (y), y being measured as the height in Tab Zone B at the outboard edge of the stretch member, is such that x is greater than or equal to y.

64. The fastening system according to claim 63, wherein x is greater than y.

65. The fastening system according to claim 35, obtained by the process of:

(d) advancing a roll of stretch member material in the MD;

(e) splaying a release tape/closure member sandwich and engaging the splayed sandwich such that the release tape portion of the sandwich is disposed below the vertical plane of the elastic/stretch member material and the closure member portion of the sandwich is disposed above such vertical plane; and then (f) die-cutting the shape of the stretch member, causing the closure member or release tape, to take on the same shape as the upper or lower edge of the stretch member, respectively;

wherein for step (b), the closure member overlaps and extends beyond the upper edge of the elastic/stretch member's profile to be die-cut in step (c), and the release tape overlaps and extends beyond the lower edge of the elastic/stretch member's profile to be die-cut in step (c).

66. An absorbent article comprising the fastening system according to claim 35.

67. The absorbent article according to claim 66, wherein the absorbent article is selected from diapers, training pants, adult incontinence undergarments, and feminine hygiene products.

68. The absorbent article according to claim 66, wherein the absorbent article is a diaper or training pant.

* * * * *